US008178679B2

(12) United States Patent
Matassa et al.

(10) Patent No.: US 8,178,679 B2
(45) Date of Patent: May 15, 2012

(54) DERIVATIVES OF 4-(2-AMINO-1-HYDROXYETHYL)PHENOL AS AGONISTS OF THE β2 ADRENERGIC RECEPTORS

(75) Inventors: Victor Giulio Matassa, La Floresta (ES); Carlos Puig Duran, Barcelona (ES); Maria Prat Quiñones, Barcelona (ES); Laia Sole Feu, Esplugues de Llobregat (ES); Oriol Llera Soldevila, Girona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 12/745,195

(22) PCT Filed: Nov. 10, 2008

(86) PCT No.: PCT/EP2008/009469
§ 371 (c)(1),
(2), (4) Date: May 27, 2010

(87) PCT Pub. No.: WO2009/068177
PCT Pub. Date: Jun. 4, 2009

(65) Prior Publication Data
US 2010/0324000 A1    Dec. 23, 2010

(30) Foreign Application Priority Data
Nov. 28, 2007 (ES) .................. 200703157

(51) Int. Cl.
*C07D 215/26* (2006.01)
*C07C 233/43* (2006.01)
*C07C 215/34* (2006.01)
(52) U.S. Cl. .............. 546/157; 564/220; 564/364
(58) Field of Classification Search ............ None
See application file for complete search history.

(56) References Cited

U.S. PATENT DOCUMENTS

| | | |
|---|---|---|
| 3,007,923 A | 11/1961 | Muller et al. |
| 3,053,865 A | 9/1962 | Metuchen et al. |
| 3,104,246 A | 9/1963 | Amiard et al. |
| 3,678,137 A | 7/1972 | Pfeiffer et al. |
| 3,929,768 A | 12/1975 | Brattsand et al. |
| 3,970,677 A | 7/1976 | Nishimura et al. |
| 3,975,391 A | 8/1976 | Nakagawa et al. |
| 3,994,901 A | 11/1976 | Nakagawa et al. |
| 4,022,776 A | 5/1977 | Nakagawa et al. |
| 4,022,784 A | 5/1977 | Nakagawa et al. |
| 4,026,897 A | 5/1977 | Nakagawa et al. |
| 4,068,076 A | 1/1978 | Nakagawa et al. |
| 4,145,542 A | 3/1979 | Nakagawa et al. |
| 4,753,962 A | 6/1988 | Ainsworth et al. |
| 4,992,474 A | 2/1991 | Skidmore et al. |
| 4,997,986 A | 3/1991 | Mitchell et al. |
| 5,099,068 A | 3/1992 | Mitchell et al. |
| 5,109,023 A | 4/1992 | Mitchell et al. |
| 5,201,308 A | 4/1993 | Newhouse |
| 5,263,475 A | 11/1993 | Altermatt et al. |
| 5,283,262 A | 2/1994 | Mitchell et al. |
| 5,435,301 A | 7/1995 | Herold et al. |
| 5,482,934 A | 1/1996 | Calatayud et al. |
| 5,507,281 A | 4/1996 | Kuhnel et al. |
| 5,617,845 A | 4/1997 | Poss et al. |
| 5,685,294 A | 11/1997 | Gupte et al. |
| 6,541,669 B1 | 4/2003 | Moran et al. |
| 7,498,321 B2 | 3/2009 | Biggadike et al. |
| 7,964,615 B2 | 6/2011 | Puig Duran et al. |
| 2002/0055651 A1 | 5/2002 | Moran et al. |
| 2003/0136405 A1 | 7/2003 | Goede et al. |
| 2003/0153597 A1 | 8/2003 | Moran et al. |
| 2004/0059116 A1 | 3/2004 | Moran et al. |
| 2004/0167167 A1 | 8/2004 | Mammen et al. |
| 2005/0043337 A1 | 2/2005 | Rito et al. |
| 2005/0159448 A1 | 7/2005 | McKinnell et al. |
| 2005/0192316 A1 | 9/2005 | Moran et al. |
| 2005/0215590 A1 | 9/2005 | Brown et al. |
| 2005/0272769 A1 | 12/2005 | Linsell |
| 2006/0019991 A1 | 1/2006 | McKinnell et al. |
| 2006/0035931 A1 | 2/2006 | Chao et al. |
| 2006/0081246 A1 | 4/2006 | Goede et al. |
| 2006/0178410 A1 | 8/2006 | Moran et al. |
| 2006/0205949 A1 | 9/2006 | Dalziel et al. |
| 2007/0197536 A1 | 8/2007 | Dal Piaz et al. |
| 2009/0042933 A1 | 2/2009 | Duran et al. |
| 2009/0082378 A1 | 3/2009 | Duran et al. |
| 2010/0093681 A1 | 4/2010 | Duran et al. |
| 2010/0168161 A1 | 7/2010 | Tanā et al. |
| 2011/0028442 A1 | 2/2011 | Puig Duran et al. |

(Continued)

FOREIGN PATENT DOCUMENTS
DE    2 236 272    2/1973
(Continued)

OTHER PUBLICATIONS

Vippagunta et al., Crystalline solids, 48 Adv. Drug Delivery Rev. 3-26 (2001).*
Silverman, The Organic Chemistry of Drug Design and Drug Action, Academic Press (1992).*
International Search Report for International Application No. PCT/EP2008/009469, dated May 7, 2009.
U.S. Appl. No. 11/920,561, filed Feb. 11, 2008, Puig Duran et al.
U.S. Appl. No. 12/298,131, filed Oct. 22, 2008, Puig Duran et al.
U.S. Appl. No. 12/444,935, filed Apr. 9, 2009, Bach Tana et al.
U.S. Appl. No. 12/526,090, filed Oct. 9, 2009, Puig Duran et al.
U.S. Appl. No. 12/919,134, filed Aug. 24, 2010, Puig Duran et al.
Bastin, RD et al. "Salt Selection and Optimisation for Pharmaceutical New Chemical Entities," Organic Process Research and Development, 4(5): 427-435 (2000).

(Continued)

*Primary Examiner* — Janet Andres
*Assistant Examiner* — Timothy R Rozof
(74) *Attorney, Agent, or Firm* — Finnegan, Henderson, Farabow, Garrett & Dunner, LLP

(57) ABSTRACT

The present disclosure relates to 4-(2-amino-1-hydroxyethyl)phenol derivatives of formula (I) as well as pharmaceutical compositions comprising them, and their use in therapy as agonists of the β2 adrenergic receptor.

13 Claims, 2 Drawing Sheets

U.S. PATENT DOCUMENTS

| | | |
|---|---|---|
| 2011/0251165 A1 | 10/2011 | Puig Duran et al. |
| 2011/0251166 A1 | 10/2011 | Puig Duran et al. |
| 2011/0251234 A1 | 10/2011 | Carrera Carrera et al. |

FOREIGN PATENT DOCUMENTS

| | | |
|---|---|---|
| DE | 2 310 140 | 9/1974 |
| DE | 2 461 861 | 8/1975 |
| DE | 4 239 402 | 5/1994 |
| EP | 0 069 715 | 1/1983 |
| EP | 0 147 719 | 7/1985 |
| EP | 0 166 294 | 1/1986 |
| EP | 0 286 242 | 10/1988 |
| EP | 0 317 206 | 5/1989 |
| EP | 0 424 790 | 5/1991 |
| EP | 0 505 321 | 9/1992 |
| EP | 0 674 533 | 10/1995 |
| EP | 1 078 629 | 2/2001 |
| EP | 1 235 787 | 9/2002 |
| EP | 1 577 291 | 9/2005 |
| ES | 2 232 306 | 5/2005 |
| GB | 0 869 511 | 5/1961 |
| GB | 1 200 886 | 8/1970 |
| GB | 1 247 370 | 9/1971 |
| GB | 1 458 251 | 12/1976 |
| GB | 1 468 156 | 12/1976 |
| GB | 2 041 763 | 9/1980 |
| GB | 2 140 800 | 12/1984 |
| GB | 2 160 863 | 1/1986 |
| GB | 2 165 159 | 4/1986 |
| GB | 2 242 134 | 9/1991 |
| JP | 51 149 282 | 12/1976 |
| JP | 59 093 051 | 5/1984 |
| WO | WO 91/02558 | 3/1991 |
| WO | WO 91/14468 | 10/1991 |
| WO | WO 92/00771 | 1/1992 |
| WO | WO 92/03175 | 3/1992 |
| WO | WO 92/04068 | 3/1992 |
| WO | WO 92/04928 | 4/1992 |
| WO | WO 92/09322 | 6/1992 |
| WO | WO 96/32150 | 10/1996 |
| WO | WO 97/00703 | 1/1997 |
| WO | WO 97/12687 | 4/1997 |
| WO | WO 98/09632 | 3/1998 |
| WO | WO 99/30703 | 6/1999 |
| WO | WO 99/64035 | 12/1999 |
| WO | WO 01/36375 | 5/2001 |
| WO | WO 01/042193 | 6/2001 |
| WO | WO 02/066422 | 8/2002 |
| WO | WO 02/070490 | 9/2002 |
| WO | WO 02/092606 | 11/2002 |
| WO | WO 03/000325 | 1/2003 |
| WO | WO 03/042160 | 5/2003 |
| WO | WO 03/061742 | 7/2003 |
| WO | WO 03/072539 | 9/2003 |
| WO | WO 03/091204 | 11/2003 |
| WO | WO 03/097613 | 11/2003 |
| WO | WO 03/099764 | 12/2003 |
| WO | WO 2004/011416 | 2/2004 |
| WO | WO 2004/016578 | 2/2004 |
| WO | WO 2004/058729 | 7/2004 |
| WO | WO 2004/089892 | 10/2004 |
| WO | WO 2004/106279 | 12/2004 |
| WO | WO 2005/030678 | 4/2005 |
| WO | WO 2005/049581 | 6/2005 |
| WO | WO 2005/121065 | 12/2005 |
| WO | WO 2005/123692 | 12/2005 |
| WO | WO 2005/123693 | 12/2005 |
| WO | WO 2006/023457 | 3/2006 |
| WO | WO 2006/051375 | 5/2006 |
| WO | WO 2006/122788 | 11/2006 |
| WO | WO 2007/124898 | 11/2007 |
| WO | WO 2008/046598 | 4/2008 |
| WO | WO 08/095720 | 8/2008 |
| WO | WO 2009/106351 | 9/2009 |
| WO | WO 2010/072354 | 7/2010 |
| WO | WO 2010/094483 | 8/2010 |
| WO | WO 2010/094484 | 8/2010 |
| WO | WO 2010/102831 | 9/2010 |

OTHER PUBLICATIONS

CAPLUS English Abstract of DE 2 236 272, Accession No. 1973:405128.
CAPLUS English Abstract of DE 2 310 140, Accession No. 1975:31115.
CAPLUS English Abstract of JP 51 149 282, Accession No. 1977:468184.
CAPLUS English Abstract of JP 59 093 051, Accession No. 1985:45790.
CAPLUS English Abstract of journal article by Meglio, P. et al. Accession No. 1980:426036.
Coleman, R.A. et al. "Novel and Versatile Superfusion System," *Journal of Pharmacological Methods*, 21: 71-86 (1989).
Cortijo, J. et al. "Effects of dantrolene on the responses to methylxanthines in the isolated guinea-pig trachea," European Journal of Pharmacology 198: 171-176 (1991).
Curran, P.K. et al. "Endogenous $\beta_3$-But Not $\beta_1$-Adrenergic Receptors Are Resistant to Agonist-Mediated Regulation in Human SK-N-MC Neurotumor Cells," *Cell. Signal.*, 8(5): 355-364 (1996).
Deyrup, M.D. et al. "Structure-affinity profile of 8-hydroxycarbostyril-based agonists that dissociate slowly from the $\beta_2$-adrenoceptor," Naunyn-Schmiedeberg's Archives of Pharmacology, 359: 168-177(1999).
English Abstract of WO 2002/92606, dated Nov. 21, 2002.
Furuie, H. et al. "Suppressive effect of novel phosphodiesterase4 (PDE4) inhibitor ONO-6126 on TNF-$\alpha$ release was increased after repeated oral administration in healthy Japanese subjects," *Eur. Resp. Journal*, 22(Supp. 45):Abstract 2557 (2003).
Ismail, FMD. "Important fluorinated drugs in experimental and clinical use," Journal of Fluorine Chemistry 118:27-33 (2002).
Hart, D.J. "A Synthesis of (±)-Gephyrotoxin," *Journal of Organic Chemistry*, 46:3576-3578 (1981).
Hart, D.J. et al. "Total Syntheses of *dl*-Gephyrotoxin and *dl*-Dihydrogephyrotoxin," *J. American Chem. Society*, 105(5): 1255-1263 (1983).
Hashima, H. et al. "Synthesis and Biological Activities of the Marine Byrozoan Alkaloids Convolutamines A, C and F, and Lutamides A and C," *Bioorganic & Medicinal Chemistry*, 8: 1757-1766 (2000).
Hett, R. et al. "Enantioselective Synthesis of Salmeterol via Asymmetric Borane Reduction," *Tetrahedron Letters*, 35(50): 9375-9378 (1994).
Hett, R. et al. "Large-Scale Synthesis of Enantio- and Diastereomerically Pure (*R,R*)-Formoterol," *Organic Process Research & Development*, 2(2): 96-99 (1998).
International Search Report mailed Sep. 12, 2006, for International Application No. PCT/EP2006/004680 (WO 2006/122788 A1).
International Search Report mailed Jun. 21, 2007, for International Application No. PCT/EP2007/003601 (WO 2007/124898 A1).
International Search Report mailed Mar. 19, 2008, for International Application No. PCT/EP2007/008992 (WO 2008/046598 A1).
International Search Report mailed May 28, 2008, for International Application No. PCT/EP2008/000975 (WO 2008/095720).
International Search Report mailed Apr. 21, 2009, for International Application No. PCT/EP2009/001431 (WO 2009/106351).
Interview Summary for U.S. Appl. No. 11/920,561, dated Jun. 11, 2010.
Kaiser, C. et al. "Adrenergic Agents. 1. Synthesis and Potential $\beta$-Adrenergic Agonist Activity of Some Catecholamine Analogs Bearing a Substituted Amino Functionality in the Meta Position," *Journal of Medicinal Chemistry*, 17(1): 49-57 (1974).
Meglio, P. et al. "Synthesis and pharmacological study of orciprenaline and salbutamol derivatives," Farmaco, Edizione Scientifica, 35(3): 203-230 (1980).
Meyers, A.I. et al. "Oxazolines. XI. Synthesis of Functionalized Aromatic and Aliphatic Acids. A Useful Protecting Group for Carboxylic Acids against Grignard and Hydride Reagents," *Journal of Organic Chemistry*, 39(18): 2787-2793 (1974).

Meyers, A.I. et al. "Substitutions on 1-Methoxynaphthalenes via their Oxazoline Derivatives: A Convenient Route to 1-Substituted Naphthoic Acids," *Synthesis Communications*, 2:105-107 (1983).

Murase, K. et al. "New β-Adrenoreceptor Stimulants. Studies on 3-Acylamino-4-hydroxy-α-(N-substituted aminomethyl)benzyl Alcohols," *Chem. Pharm. Bull.*, 25(6): 1368-1377 (1977).

Nielsen, K.G. et al. "Flow-dependent effect of formoterol dry-powder inhaled from the Aerolizer®," *Eur. Respir. Journal*, 10: 2105-2109 (1997).

Office Action for U.S. Appl. No. 11/920,561, dated Jun. 2, 2010.

Portoghese, P.S. "Stereochemical Studies on Medicinal Agents. 19. X-Ray Crystal Structures of Two (±)-Allylprodine Diastereomers. The Role of the Allyl Group in Conferring High Stereoselectivity and Potency at Analgetic Receptors," *Journal of Medicinal Chemistry*, 19(1): 55-57 (1976).

Restriction Requirement for U.S. Appl. No. 11/920,561, dated Mar. 16, 2010.

Smart, BE. "Fluorine substituent effects (on bioactivity)," Journal of Fluorine Chemistry 109:3-11 (2001).

Sterling, J. et al. "Novel Dual Inhibitors of AChE and MAO Derived from Hydroxy Aminoindan and Phenethylamine as Potential Treatment for Alzheimer's Disease," *J. Med. Chem.* 45(24): 5260-5279 (2002).

Svenson, R. et al. "On the Hydrozirconation of Some Long-Chain Unsaturated Fatty Acid Oxazolines," *Chemica Scripta.*, 19: 149-153 (1982).

Yang, Z. et al. "A Novel and Practical Method for the Preparation of α,α-Difluoro Functionalized Esters," *J. Chem. Soc., Chem. Commun.*, 3: 233-234 (1992).

Yang, Z. "Synthesis of new α,α,β,β-tetrafluoroesters," *Journal of Fluorine Chemistry*, 125: 763-765 (2004).

Yoshizaki, S. et al. "Sympathomimetic Amines having a 3,4-Dihydrocarbostyril Nucleus," Chemical and Pharmaceutical Bulletin, 26(5): 1611-1614 (1978).

Yoshizaki, S. et al. "Sympathomimetic Amines Having a Carbostyril Nucleus," *Journal of Medicinal Chemistry*, 19(9): 1138-1142 (1976).

International Search Report for PCT/EP2009/008970 (WO 2010/072354) dated Mar. 2, 2010.

Morissette, SL et al. "High-Throughput Crystallization: Polymorphs, Salts, Co-Crystals and Solvates of Pharmaceutical Solids," Advanced Drug Delivery Reviews, 56: 275-300 (2004).

Notice of Allowance dated Jan. 26, 2011 in U.S. Appl. No. 11/920,561.

Office Action (Quayle Action) dated Nov. 9, 2010 in U.S. Appl. No. 11/920,561.

Office Action dated Apr. 25, 2011 in U.S. Appl. No. 12/298,131.

Restriction Requirement dated May 13, 2011 in U.S. Appl. No. 12/444,935.

Dexamethasone, Merck Index, Monograph No. 02943 (2011).

International Search Report mailed Sep. 16, 2010, for International Application No. PCT/EP2010/001582 (WO 2010/102831).

U.S. Appl. No. 13/255,261, filed Sep. 9, 2011, Marchueta Hereu et al.

U.S. Appl. No. 13/141,156, filed Jun. 21, 2011, Carerra Carerra et al.

U.S. Appl. No. 13/202,020, filed Aug. 17, 2011, Ruf et al.

U.S. Appl. No. 13/202,025, filed Aug. 17, 2011, Ruf et al.

Han, J. "Advances in characterization of pharmaceutical hydrates," *Trends in Bio/Pharmaceutical Industry*, 3:25-29 (2006).

International Search Report for International Application No. PCT/EP2010/001027 (WO 2010/094484), mailed May 25, 2010.

International Search Report for International Application No. PCT/EP2010/001026 (WO 2010/094483), mailed May 27, 2010.

Johnson, M., "Salmeterol," *Medical Research Reviews*, 15(3):225-257 (1995).

Kikkowa, H. et al., "Differential contribution of two seine residues of wild type and constitutively active $β_2$- adrenorectors to the interaction with $β_2$-selective agonists," *British Journal of Pharmacology*, 121:1059-1064 (1997).

Office Action for U.S. Appl. No. 12/444,935, dated Jul. 7, 2011.

Office Action for U.S. Appl. No. 12/526,090, dated Oct. 14, 2011.

Patani, G.A. et al., "Bioisosterism: a rational approach in drug design," *Chem. Rev,.* 96: 314-3176 (1996).

Restriction Requirement for U.S. Appl. No. 12/526,090, dated Jul. 20, 2011.

STN Search Report, Accession No. 2003:875242, CAS RN 620599-83-9 (2011).

Williams, D.A. et al., FOYE's Principles of Medicinal Chemistry, 5th Edition, pp. 59-63 (2002).

Office Action (Restriction Requirement) dated Dec. 29, 2011 in U.S. Appl. No. 13/094,156.

Office Action dated Jan. 26, 2012 in U.S. Appl. No. 12/298,13.

Office Action dated Jan. 30, 2012 in U.S. Appl. No. 12/444,935.

* cited by examiner

DERIVATIVES OF 4-(2-AMINO-1-HYDROXYETHYL)PHENOL AS AGONISTS OF THE β2 ADRENERGIC RECEPTORS

This application is a national stage filing under 35 U.S.C. §371 of International Application No. PCT/EP2008/009469 filed on 10 Nov. 2008, which claims priority of Spanish Patent Application No. P200703157, filed on 28 Nov. 2007. The contents of both applications are incorporated herein by reference.

FIELD OF THE INVENTION

The present invention is directed to novel β2 adrenergic receptor agonists. The invention is also directed to pharmaceutical compositions comprising such compounds, methods of using such compounds to treat diseases associated with β2 adrenergic receptor activity, and processes and intermediates useful for preparing such compounds.

BACKGROUND OF THE INVENTION

β2 adrenergic receptor agonists are recognized as effective drugs for the treatment of pulmonary diseases such as asthma and chronic obstructive pulmonary disease (including chronic bronchitis and emphysema). β2 adrenergic receptor agonists are also useful for treating pre-term labor, glaucoma and are potentially useful for treating neurological disorders and cardiac disorders.

In spite of the success that has been achieved with certain β2 adrenergic receptor agonists, current agents possess less than desirable potency, selectivity, onset, and/or duration of action. Thus, there is a need for additional β2 adrenergic receptor agonists having improved properties. Preferred agents may possess, among other properties, improved potency, selectivity, onset, improved safety margins, improved therapeutic window and/or duration of action.

SUMMARY OF THE INVENTION

Figure 1:
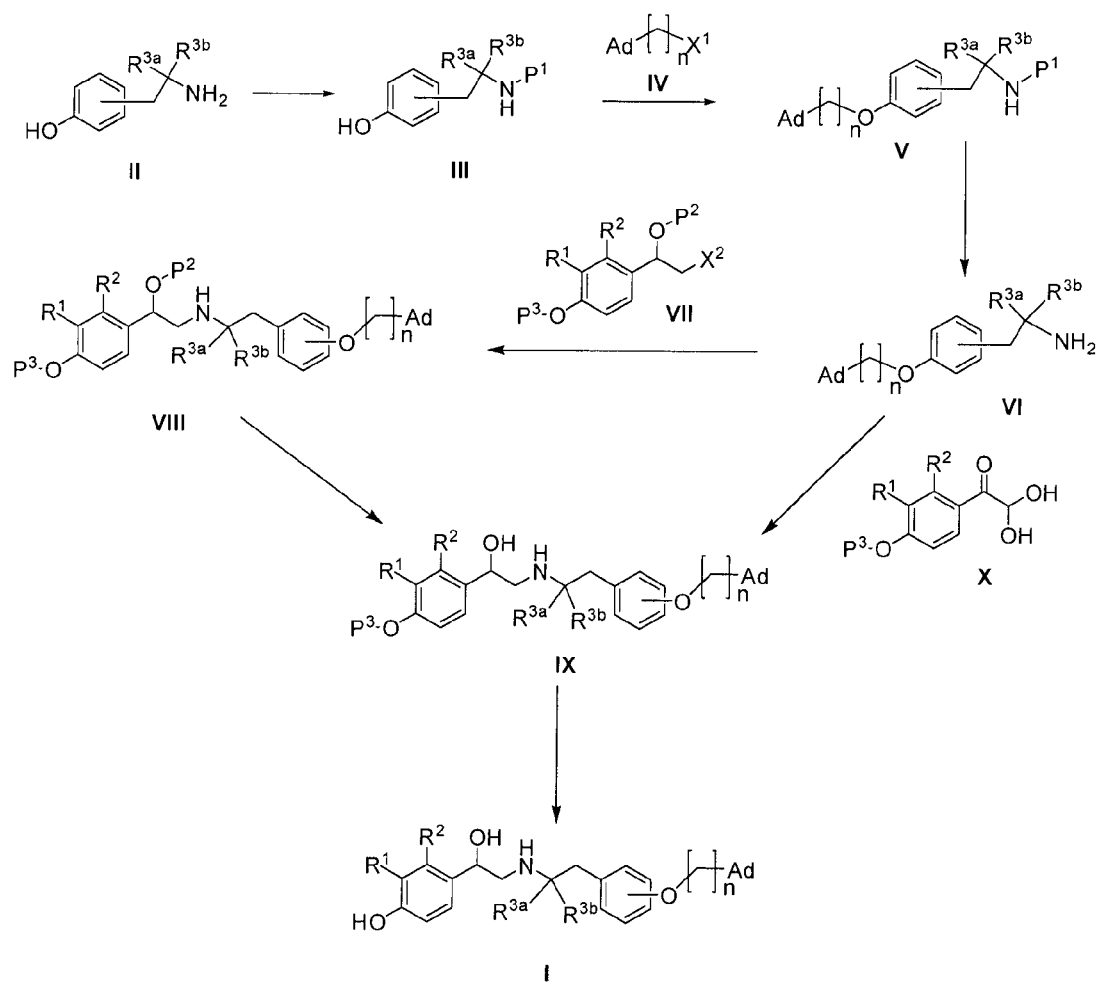
FIG. 1 shows a process for preparing compounds of formula (I) in accordance with embodiments described in this application.

The invention provides novel compounds that possess β2 adrenergic receptor agonist activity. Accordingly, there is provided a compound of the invention which is of formula (I):

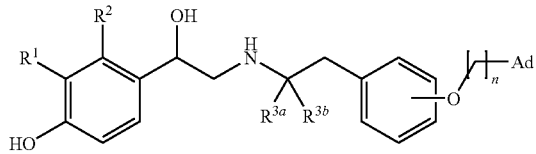

Formula (I)

wherein:
$R^1$ is selected from the group consisting of —$CH_2OH$ and —NH(CO)H groups, and
$R^2$ represents a hydrogen atom; or $R^1$ together with $R^2$ form the group —NH—C(O)—CH=CH—, wherein the nitrogen atom is bound to the carbon atom in the phenyl ring holding $R^1$ and the carbon atom is bound to the carbon atom in the phenyl ring holding $R^2$;
$R^{3a}$ and $R^{3b}$ are independently selected from the group consisting of hydrogen atoms and $C_{1-4}$ alkyl groups
n represents an integer from 1 to 3;
Ad represents 1-adamantyl or 2-adamantyl group
or a pharmaceutically-acceptable salt or solvate or stereoisomer thereof.

The invention also provides a pharmaceutical composition comprising a compound of the invention and a pharmaceutically-acceptable carrier. The invention further provides combinations comprising a compound of the invention and one or more other therapeutic agents and pharmaceutical compositions comprising such combinations.

The invention also provides a method of treating a disease or condition associated with β2 adrenergic receptor activity (e.g. a pulmonary disease, such as asthma or chronic obstructive pulmonary disease, pre-term labor, glaucoma, a neurological disorder, a cardiac disorder, or inflammation) in a mammal, comprising administering to the mammal, a therapeutically effective amount of a compound of the invention. The invention further provides a method of treatment comprising administering a therapeutically effective amount of a combination of a compound of the invention together with one or more other therapeutic agents.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with β2 adrenergic receptor activity (e.g. a pulmonary disease, such as asthma or chronic obstructive pulmonary disease, pre-term labor, glaucoma, a neurological disorder, a cardiac disorder, or inflammation) in a mammal.

DETAILED DESCRIPTION OF THE INVENTION

When describing the compounds, compositions and methods of the invention, the following terms have the following meanings, unless otherwise indicated.

The term "therapeutically effective amount" refers to an amount sufficient to effect treatment when administered to a patient in need of treatment.

The term "treatment" as used herein refers to the treatment of a disease or medical condition in a human patient which includes:

(a) preventing the disease or medical condition from occurring, i.e., prophylactic treatment of a patient;
(b) ameliorating the disease or medical condition, i.e., causing regression of the disease or medical condition in a patient;
(c) suppressing the disease or medical condition, i.e., slowing the development of the disease or medical condition in a patient; or
(d) alleviating the symptoms of the disease or medical condition in a patient.

The phrase "disease or condition associated with β2 adrenergic receptor activity" includes all disease states and/or conditions that are acknowledged now, or that are found in the future, to be associated with β2 adrenergic receptor activity. Such disease states include, but are not limited to, pulmonary diseases, such as asthma and chronic obstructive pulmonary disease (including chronic bronchitis and emphysema), as well as neurological disorders and cardiac disorders. β2 adrenergic receptor activity is also known to be associated with pre-term labor (see International Patent Application Publication Number WO 98/09632), glaucoma and some types of inflammation (see International Patent Application Publication Number WO 99/30703 and Patent Application Publication Number EP 1 078 629).

As used herein the term $C_{1-4}$ alkyl embraces optionally substituted, linear or branched radicals having 1 to 4 carbon atoms. Examples include methyl, ethyl, n-propyl, i-propyl, n-butyl, sec-butyl, t-butyl, A said optionally substituted alkyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, substituents on an alkyl group are themselves unsubstituted. Preferred optionally substituted alkyl groups are unsubstituted or substituted with 1, 2 or 3 fluorine atoms.

The term "pharmaceutically-acceptable salt" refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

Salts derived from pharmaceutically-acceptable acids include acetic, benzenesulfonic, benzoic, camphosulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid), napadisilic (1,5-naphthalenedisulfonic acid) and the like. Particularly preferred are salts derived from fumaric, hydrobromic, hydrochloric, acetic, sulfuric, methanesulfonic, xinafoic, and tartaric acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts.

Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

The term "solvate" refers to a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate of stereoisomer thereof" is intended to include all permutations of salts, solvates and stereoisomers, such as a solvate of a pharmaceutically-acceptable salt of a stereoisomer of a compound of formula (I).

The term "amino-protecting group" refers to a protecting group suitable for preventing undesired reactions at an amino nitrogen. Representative amino-protecting groups include, but are not limited to, formyl; acyl groups, for example alkanoyl groups such as acetyl; alkoxycarbonyl groups such as tert-butoxycarbonyl (Boc); arylmethoxycarbonyl groups such as benzyloxycarbonyl (Cbz) and 9-fluorenylmethoxycarbonyl (Fmoc); arylmethyl groups such as benzyl (Bn), trityl (Tr), and 1,1-di-(4'-methoxyphenyl)methyl; silyl groups such as trimethylsilyl (TMS) and tert-butyldimethylsilyl (TBS); and the like.

The term "hydroxy-protecting group" refers to a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

The compounds of the invention contain at least a chiral center. Accordingly, the invention includes racemic mixtures, enantiomers, and mixtures enriched in one or more stereoisomer. The scope of the invention as described and claimed encompasses the racemic forms of the compounds as well as the individual enantiomers, diastereomers, and stereoisomer-enriched mixtures.

In an embodiment of the present invention, $R^1$ represents a —NH(CO)H group, and $R^2$ represents a hydrogen atom; or $R^1$ together with $R^2$ form the group —NH—C(O)—CH=CH—, wherein the nitrogen atom is bound to the carbon atom in the phenyl ring holding $R^1$ and the carbon atom is bound to the carbon atom in the phenyl ring holding $R^2$. More preferably, $R^1$ together with $R^2$ form the group —NH—C(O)—CH=CH—, wherein the nitrogen atom is bound to the carbon atom in the phenyl ring holding $R^1$ and the carbon atom is bound to the carbon atom in the phenyl ring holding $R^2$ In another embodiment of the present invention, $R^{3a}$ and $R^{3b}$ are independently selected from the group consisting of hydrogen atoms and methyl groups. More preferably $R^{3a}$ represents a hydrogen atom and $R^{3b}$ is selected from the group consisting of hydrogen atoms and methyl groups In still another embodiment of the compounds of formula (I), n has a value of 1 or 2, more preferably n has a value of 2.

In another embodiment, the present invention provides compounds of formula (IA):

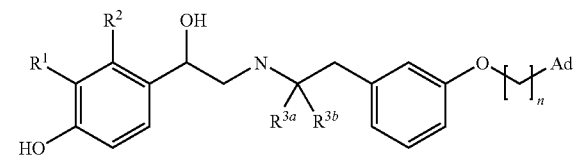

(IA)

In yet another embodiment, the present invention provides compounds of formula (IA) wherein $R^1$ together with $R^2$ form the group —NH—C(O)—CH=CH—, wherein the nitrogen atom is bound to the carbon atom in the phenyl ring holding $R^1$ and the carbon atom is bound to the carbon atom in the phenyl ring holding $R^2$, $R^{3a}$ and $R^{3b}$ are independently selected from the group consisting of hydrogen atoms and methyl groups and n has a value of 2.

Particular individual compounds of the invention include:

5-{(1R)-2-[((1R,S)-2-{3-[2-(1-adamantyl)ethoxy]phenyl}-1-methylethyl)amino]-1-hydroxyethyl}-8-hydroxyquinolin-2(1H)-one 5-{(1R)-2-[(2-{4-[2-(1-adamantyl)ethoxy]phenyl}-1-methylethy)amino]-1-hydroxyethyl}-8-hydroxyquinolin-2(1H)-one 5-{(1R)-2-[(2-{4-[2-(1-adamantyl)ethoxy]phenyl}ethyl)amino]-1-hydroxyethyl}-8-hydroxyquinolin-2(1H)-one (5-{(1R)-2-[(2-{4-[2-(1-adamantyl)ethoxy]phenyl}ethyl)amino]-1-hydroxyethyl}-2-hydroxyphenyl)formamide 4-{2-[(2-{4-[2-(1-adamantyl)ethoxy]phenyl}ethyl)amino]-1-hydroxyethyl}-2-(hydroxymethyl)phenol 5-{(1R)-2-[(2-{3-[2-(1-adamantyl)ethoxy]phenyl}ethyl)amino]-1-hydroxyethyl}-8-hydroxyquinolin-2(1H)-one 5-[(1R)-2-({2-[4-(1-adamantylmethoxy)phenyl]ethyl}amino)-1-hydroxyethyl]-8-hydroxyquinolin-2(1H)-one 5-[(1R)-2-({2-[3-(1-adamantylmethoxy)phenyl]ethyl}amino)-1-hydroxyethyl]-8-hydroxyquinolin-2(1H)-one 5-{(1R)-2-[(2-{4-[3-(1-adamantyl)propoxy]phenyl}ethyl)amino]-1-hydroxyethyl}-8-hydroxyquinolin-2(1H)-one 5-{(1R)-2-[(2-{3-[3-(1-adamantyl)propoxy]phenyl}ethyl)amino]-1-hydroxyethyl}-8-hydroxyquinolin-2(1H)-one (5-{(1R)-2-[(2-{3-[2-(1-adamantyl)ethoxy]phenyl}ethyl)amino]-1-hydroxyethyl}-2-hydroxyphenyl)formamide (5-{(1R)-2-[((1R)-2-{3-[2-(1-adamantyl)ethoxy]phenyl}-1-methylethyl)amino]-1-hydroxyethyl}-2-hydroxyphenyl)formamide 5-{(1R)-2-[((1R)-2-{3-[2-(1-adamantyl)ethoxy]phenyl}-1-methylethyl)amino]-1-hydroxyethyl}-8-hydroxyquinolin-2(1H)-one 5-{(1R)-2-[(2-{4-[2-(2-adamantyl)ethoxy]phenyl}ethyl)amino]-1-hydroxyethyl}-8-hydroxyquinolin-2(1H)-one 5-[(1R)-2-({2-[3-(2-adamantylethoxy)phenyl]ethyl}amino)-1-hydroxyethyl]-8-hydroxyquinolin-2(1H)-one 4-{(1R)-2-[((1R)-2-{3-[2-(1-adamantyl)ethoxy]phenyl}-1-methylethyl)amino]-1-hydroxyethyl}-2-(hydroxymethyl)phenol 5-{(1R)-2-[(2-{3-[2-(1-adamantyl)ethoxy]phenyl}-1,1-dimethylethyl)amino]-1-hydroxyethyl}-8-hydroxyquinolin-2(1H)-one and pharmaceutically-acceptable salts and solvates thereof.

Of particular interest are the compounds:

5-{(1R)-2-[((1R,S)-2-{3-[2-(1-adamantyl)ethoxy]phenyl}-1-methylethyl)amino]-1-hydroxyethyl}-8-hydroxyquinolin-2(1H)-one 5-{(1R)-2-[(2-{3-[2-(1-adamantyl)ethoxy]phenyl}ethyl)amino]-1-hydroxyethyl}-8-hydroxyquinolin-2(1H)-one 5-[(1R)-2-({2-[3-(1-adamantylmethoxy)phenyl]ethyl}amino)-1-hydroxyethyl]-8-hydroxyquinolin-2(1H)-one 5-{(1R)-2-[(2-{3-[3-(1-adamantyl)propoxy]phenyl}ethyl)amino]-1-hydroxyethyl}-8-hydroxyquinolin-2(1H)-one 5-{(1R)-2-[((1R)-2-{3-[2-(1-adamantyl)ethoxy]phenyl}-1-methylethyl)amino]-1-hydroxyethyl}-8-hydroxyquinolin-2(1H)-one 5-[(1R)-2-({2-[3-(2-adamantylethoxy)phenyl]ethyl}amino)-1-hydroxyethyl]-8-hydroxyquinolin-2(1H)-one The invention comprises also pharmaceutical compositions comprising a therapeutically effective amount of a compound as hereinabove defined and a pharmaceutically acceptable carrier.

In an embodiment of the present invention the pharmaceutical composition further comprises a therapeutically effective amount of one or more other therapeutic agents.

It is also an embodiment of the present invention that the pharmaceutical composition is formulated for administration by inhalation.

The compounds of the present invention as hereinabove defined may also be combined with one or more other therapeutic agents, in particular one or more drugs selected from the group consisting of corticosteroids, an antichlolinergic agents and PDE4 inhibitors.

In a preferred embodiment of the present invention the combination comprises a compound of formula (I) as hereinabove defined and a drug selected from the group consisting of fluticasone propionate, 6α, 9α-difluoro-17α-[-(2-furanylcarbonyl)oxy]-11β-hydroxy-16α-methyl-3-oxo-androsta-1,4-diene-17β-carbothioic acid S-fluoromethyl ester, and 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, mometasone furoate, 3(R)-(2-hydroxy-2,2-dithien-2-ylacetoxy)-1-(3-phenoxypropyl)-1-azoniabicyclo[2.2.2]octane bromide and (3R)-1-phenetyl-3-(9H-xanthene-9-carbonyloxy)-1-azoniabicyclo[2.2.2]octane bromide.

The invention is also directed to a method of treating a disease or condition in a mammal associated with β2 adrenergic receptor activity, the method comprising administering to the mammal, a therapeutically effective amount of a pharmaceutical composition comprising a β2 adrenergic receptor agonist according to the present invention. It is of particular relevance the method applied to the treatment of a disease or condition which is a pulmonary disease, preferably asthma or chronic obstructive pulmonary disease.

The method of treating a disease can also be applied within the scope of the present invention to the treatment of a disease or condition selected from the group consisting of pre-term labor, glaucoma, neurological disorders, cardiac disorders, and inflammation.

General Synthetic Procedures

The compounds of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given. Other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal are described in T. W. Greene and G. M. Wuts, Protecting Groups in Organic Synthesis, Third Edition, Wiley, New York, 1999, and references cited therein.

Processes for preparing compounds of the invention are provided as further embodiments of the invention and are illustrated by the procedures below. One of the most convenient route for the preparation of compounds of formula (I) is depicted in FIG. 1.

The amino starting compounds of formula (II) are either commercially available or known per se in the literature (see, for example, Bioorg. Med. Chem. 8 (2000), 1762; J. Med. Chem., 2002, 45 (24), 5276 and US 2005/0043337 preparation 84).

Intermediates of formula (II) are N-protected by means of, for example, t-Butyloxycarbonyl (BOC) derivative to yield intermediates of formula (III). This reaction is typically carried out by treatment of intermediates of formula (II) with diterbutyldicarbonate in neutral or basic conditions, by adding sodium hydroxide, potassium carbonate or sodium hydrogen carbonate, in a solvent such as dichloromethane, THF or dioxane at a temperature range of 0° C. to room temperature.

The protected derivatives of formula (III) are alkylated with an adamantyl derivative of formula (IV), wherein $X^1$ represents a suitable leaving group such as tosylate, mesylate, triflate or bromide, in a solvent such as THF, DMF or DMSO with the addition of a base such as cesium carbonate, potassium carbonate or sodium hydride, in a range of temperatures between room temperature and the boiling point of the solvent.

The Intermediate of formula (IV) is typically prepared from the corresponding alcohol as described in literature (see U.S. Pat. No. 3,678,137, WO 2002/092606).

The N-deprotection of Intermediates of formula (V) into the corresponding amines of formula (VI) is carried out according to the nature of the protecting group $P^1$. If $P^1$ is a BOC group, then the derivatives of formula (V) is treated with an acidic media, such as trifluoroacetic acid in dichloromethane or hydrogen chloride in dioxane, in a range of temperatures comprised between room temperature and 40° C.

Intermediates of formula (VIII) may be obtained by alkylation of the amines derivatives of formula (VI) with intermediates of formula (VII) wherein $X^2$ represents a suitable leaving group such as bromine, $P^2$ is an oxygen protecting group such as a trialkylsilyl group, and $P^3$ is also a protecting group such as benzyl or (together with $R^1$), an acetonyl radical. The reaction is carried out in a solvent such as DMF, DMSO or N-methylpyrrolidone at a temperature ranging between 80 and 150° C. in the presence of an acid scavenger such as sodium hydrogen carbonate or a tertiary amine group, with the optional addition of sodium iodide. Intermediates of formula (VII) may be prepared according to the literature (see, for ex., US2004059116, example 9C; WO2004/011416, example 2 and WO2004/016578, example 1ii).

The oxygen deprotection of intermediates of formula (VIII) leading to intermediates of formula (IX) takes place, in the case of a silyl protecting group ($P^2$), in the presence of a fluoride ion, such as, for example, tetrabutylammonium fluoride or triethylamine trihydrofluoride, in a solvent such as THF at a temperature ranging from room temperature to the boiling point of the solvent.

In an alternative way, intermediates of formula (IX) may be obtained directly by reacting intermediates of formula (VI) with glyoxal derivatives of formula (X) wherein $P^3$ is as defined above, in the presence of a reducing agent. The reaction is carried out in a solvent such as mixtures of DMSO and methanol at a temperature ranging from 0° C. to room temperature. The reducing agent may be a hydride such as sodium borohydride or sodium cyanoborohydride.

Intermediates of formula (X) are prepared as described in the literature (see, for example, EP 147719, Example 2; U.S. Pat. No. 4,753,962 Description 54 and GB 1247370, Example 1).

The deprotection of intermediates of formula (IX) giving the target compounds (I) may be carried out, in the case of an O-benzyl protection ($P^3$), by hydrogenation of intermediates of formula (IX) in a solvent such as methanol, THF or mistures of both using palladium on charcoal as a catalyst.

Figure 2:
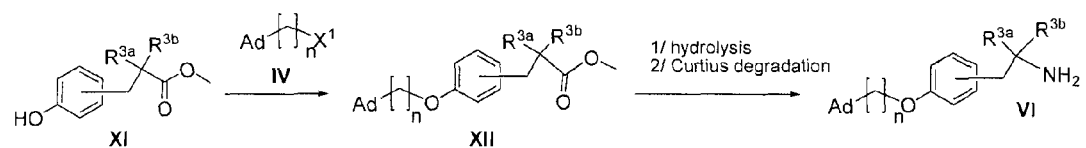
FIG. 2 shows a process for preparing intermediate amine derivatives of formula (VI)

In an alternative way as depicted in FIG. 2, the intermediate amine derivatives of formula (VI) may be prepared by alkylation of a phenol derivative of formula (XI) bearing a functional precursor, such as the carboxylic acid or ester.

The treatment of intermediates of formula (XI) with the alkylating agent of formula (IV), wherein $X^1$ is as defined before, using the same conditions described for the alkylation of intermediates of formula (III) leads to the intermediates of formula (XII). After hydrolyzing the ester functionality, typically with sodium or lithium hydroxide in alcoholic medium in a temperature ranging from room temperature to reflux, the resulting carboxylic acid may be converted to the corresponding amine derivative of formula (VI) via Curtius degradation. This reaction may be effected, inter alia, by heating to reflux in an inert solvent like toluene or xylene, an acylazide obtained for example by treatment of a mixed anhydride with sodium azide.

EXAMPLES

General. Reagents, starting materials, and solvents were purchased from commercial suppliers and used as received. Concentration refers to evaporation under vacuum using a Büchi rotatory evaporator. Reaction products were purified, when necessary, by flash chromatography on silica gel (40-63 μm) with the solvent system indicated. Spectroscopic data were recorded on a Varian Gemini 300 spectrometer and a Varian Inova 400 spectrometer. Melting points were recorded on a Büchi 535 apparatus. HPLC-MS were performed on a Gilson instrument equipped with a Gilson piston pump 321, a Gilson 864 vacuum degasser, a Gilson liquid handler 215, a Gilson 189 injection module, a Gilson Valvemate 7000, a 1/1000 splitter, a Gilson 307 make-up pump, a Gilson 170 diode array detector, and a Thermoquest Finnigan aQa detector. Semi-preparative purifications were carried out using a SunFire C18 reverse phase column (100 Å, 5 μm, 19×100 mm, purchased from WATERS).

Intermediate 1. 3-[(1E)-2-nitroprop-1-en-1-yl]phenol

To a solution of 3-hydroxybenzaldehyde (20 g, 0.16 mol) in acetic acid (40 mL) was added nitro ethane (32 mL, 0.45 mol) and ammonium acetate (8 g, 0.1 mol). The resulting mixture was stirred at 80° C. for 6 hours. The reaction mixture was poured into a solution of 400 mL of water and the precipitate was collected by filtration to obtain the title compound as a solid (23.68 g, 81%). MS (M+): 180.

Intermediate 2. 1-(benzyloxy)-3-[(1E)-2-nitroprop-1-en-1-yl]benzene

To a solution of Intermediate 1 (23.68 g, 0.13 mol) in dimethylformamide (175 mL) was slowly added sodium hydride (60%, 5.29 g, 0.13 mol). The mixture was stirred at room temperature for 1 hour. Then benzyl bromide (15.72 mL, 0.13 mol) was added into the mixture and was stirred at room temperature for 24 hours. The solvent was removed under reduced pressure. The title compound was obtained (26.46 g, 74%) and was used in the next step without further purification. MS (M+): 270.

Intermediate 3.
(1R,S)-1-[3-(benzyloxy)phenyl]propan-2-amine

A solution of Intermediate 2 (26.46 g, 0.1 mol) in tetrahydrofuran (1 L) was slowly added at 0° C. to a solution of lithium aluminium hydride (12 g, 0.32 mol) in tetrahydrofuran (180 mL). The resulting mixture was stirred at room temperature for 24 hours. Then water (12 mL), sodium hydroxide 4N (12 mL) and finally water again (36 mL) were added into the solution at 0° C. The mixture was stirred for some minutes and the resulting salts were filtered through a pad of Celite® washing with ethyl acetate (100 mL). The organic layer of the filtrate was separated from the aqueous phase, which was basified with sodium hydroxide 1N and extracted with ether, ethyl acetate and methylen chloride. The solvents were removed under reduced pressure to obtain the title compound as a white solid (14.07 g, 60%). MS (M+): 242.

Intermediate 4. tert-butyl {(1R,S)-2-[3-(benzyloxy)phenyl]-1-methylethyl}-carbamate A solution of Intermediate 3 (14.07 g, 60 mmol) in a mixture of tetrahydrofuran (200 mL) and methanol (10 mL) was slowly added to a solution of boc anhydride (13.36 g, 60 mmol) in tetrahydrofuran (50 mL). The resulting mixture was stirred at room temperature overnight. The solvents were removed under reduced pressure. The crude was dissolved in methylen chloride and the organic layer was washed several times with water. The solvent was removed under reduced pressure to obtain an oil (19.91 g; 98%) used in the next step without further purification. MS (M+): 342.

Intermediate 5. tert-butyl [(1R,S)-2-(3-hydroxyphenyl)-1-methylethyl]-carbamate To a solution of Intermediate 4 (19.91 g, 60 mmol) in methanol (350 mL) was added palladium on charcoal (10%, 1 g). The mixture was hydrogenated at 40 psi overnight. The catalyst was filtered through Celite® and the solvent removed under reduced pressure. The title compound was obtained as an oil (14.6 g; 99.1%) and used in the next step without further purification. MS (M+): 252.

Intermediate 6. 2-(1-adamantyl)ethyl 4-methylbenzenesulfonate

To a solution of 1-adamantaneethanol (3.06 g, 16.9 mmol) and triethylamine (2.8 mL, 20.1 mmol) in methylen chloride (30 mL) was added at 0° C. a suspension of 4-methylbenzene-1-sulfonyl chloride (3.88 g, 20.3 mmol) in methylen chloride (40 mL). The reaction mixture was stirred at room temperature overnight. Then, ice and a solution of ammonia 50% in water were added into the reaction mixture. The mixture was extracted with pentane and the organic layer was washed with water and brine. The solvent was removed under reduced pressure and the title compound was obtained as an oil (5.4 g, 90%). MS (M+): 335.

Intermediate 7. tert-Butyl (2-{3-[(1R,S)-2-(1-adamantyl)ethoxy]phenyl}-1-methylethyl)carbamate To a solution of Intermediate 5 (3.5 g, 11.7 mmol) in dimethylformamide (50 mL) was added a solution of intermediate 6 (5.8 g, 17.5 mmol) in dimethylformamide (50 mL) and cesium carbonate (5.7 g, 17.5 mmol). The resulting reaction mixture was stirred under argon at 50° C. overnight. The reaction mixture was poured into water and extracted with ether. The organic layer was washed with water. The solvent was removed under reduced pressure and the crude oil obtained was purified by column chromatography with silica gel, eluting with hexane/ethyl acetate (10:1) to give the title compound (4.17 g, 45%) as colourless oil. MS (M+); 414.

Intermediate 8. (1R,S)-1-{3-[2-(1-adamantyl)ethoxy]phenyl}propan-2-amine

To a solution of Intermediate 7 (5.6 g, 6.7 mmol) in dioxane (15 mL) was added hydrogen chloride (4M in dioxane, 15 mL). The reaction mixture was stirred at room temperature overnight. The solvent was removed under reduced pressure and the title compound was obtained as a white solid (1.9 g, 81%) and used in the next step without further purification. MS (M+): 349.

Intermediate 9. 5-((1R)-2-[(1R,S)-2-{3-[2-(1-adamantyl)ethoxy]phenyl}-1-methylethyl)amino]-1-{[tert-butyl(dimethyl)silyl]oxy}ethyl)-8-(benzyloxy)-quinolin-2(1H)-one To a solution of Intermediate 8 (1.54 g, 4.9 mmol) and (R)-8-(benzyloxy)-5-(2-bromo-1-(tert-butyldimethylsilyloxy)ethyl)quinolin-2(1H)-one (1.6 g, 3.2 mmol) in N-methylpyrrolidinone (6 mL) was added sodium iodide (0.74 g, 4.9 mmol) and sodium hydrogencarbonate (0.83 g, 9.8 mmol). The reaction mixture was heated at 110° C. for 6 hours and poured into water. The organic layer was extracted with ethyl acetate and washed with water and ammonium chloride. The solvent was removed under reduced pressure and the crude was purified by column chromatography with silica gel, eluting with hexane/ethyl acetate (from 3:1 to 1:1). The title compound was obtained as a solid (0.81 g, 34%) and used in the next step without further purification. MS (M+): 722.

Intermediate 10. 5-{(1R)-2-[((1R,S)-2-{3-[2-(1-adamantyl)ethoxy]phenyl}-1-methylethyl)amino]-1-hydroxyethyl}-8-(benzyloxy)quinolin-2(1H)-one To a solution of Intermediate 9 (0.81 g, 1.12 mmol) in tetrahydrofuran (9 mL) was added tetrabutylammonium fluoride (1M in tetrahydrofuran, 2 mL). The reaction mixture was stirred at room temperature overnight. The solvent was removed under reduced pressure and the crude was partitioned between methylen chloride and water. The organic layer was washed several times with water and the solvent was removed under reduced pressure. The title compound was obtained as a foam (0.68 g, 99%) and used in the next step without further purification. MS (M+): 607.

Example 1

5-{(1R)-2-[((1R,S)-2-{3-[2-(1-adamantyl)ethoxy]phenyl}-1-methylethyl)amino]-1-hydroxyethyl}-8-hydroxyquinolin-2(1H)-one

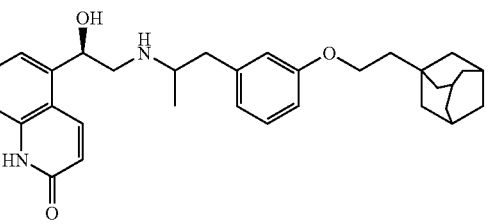

To a solution of Intermediate 10 (0.68 g, 1.12 mmol) in a mixture of methanol (30 mL) and some drops of tetrahydrofuran was added palladium on charcoal (10%, 0.07 g). The mixture was hydrogenated under a balloon pressure at room temperature overnight. The catalyst was filtered through Celite® and the solvent removed under reduced pressure. The crude was treated with ether to obtain the title compound as yellow solid (0.48 g, 85%).

$^1$H-NMR (300 MHz, dimethylsulfoxide-D6): 1.52-1.74 (bs, 17H); 1.96 (bs, 3H); 2.53-2.55 (m, 2H); 2.81-2.91 (m, 2H); 3.98-4.04 (m, 1H); 5.11 (bs, 1H); 6.56 (d, J=9.8 Hz, 1H); 6.72-6.8 (m, 4H); 6.96 (d, J=8.1 Hz, 1H); 7.11 (d, J=8.1 Hz, 1H); 7.2 (q, J=7.14 Hz, 1H); 8.2 (d, J=9 Hz, 1H).

MS (M+): 517.

Intermediate 11. 4-[(1E)-2-nitroprop-1-en-1-yl]phenol

Obtained from 4-hydroxybenzaldehyde (15 g, 0.12 mol), nitroethane (24 mL, 0.33 mol) and ammonium acetate (5.9 g, 0.08 mol) by the same procedure described in Intermediate 1 (reaction time: 20 h). The precipitate obtained was collected by filtration giving the title compound as a solid (15.4 g, 70%). MS (M+): 180.

Intermediate 12. 1-(benzyloxy)-4-[(1E)-2-nitroprop-1-en-1-yl]benzene

Obtained from Intermediate 11 (15.37 g, 90 mmol), sodium hydride (60%, 3.4 g) and benzyl bromide (10.2 g, 90 mmol) using the same procedure described in Intermediate 2. The title compound was obtained as a solid (21.3 g, 92%) and used in the next step without further purification. MS (M+): 270.

Intermediate 13. (1R,S)-1-[4-(benzyloxy)phenyl]propan-2-amine

Obtained from Intermediate 12 (21.3 g, 0.08 mmol) and lithium aluminium hydride (9 g, 0.24 mol) by the same procedure described in Intermediate 3. The title compound was obtained as a solid (19.1 g, 61%) and used in the next step without further purification. MS (M+): 242.

Intermediate 14. 4-((2R,S)-2-aminopropyl)phenol

Obtained from Intermediate 13 (11.6 g, 48 mmol) and palladium on charcoal (10%, 0.4 g) by the same procedure described in Intermediate 5. The residue obtained was crystallized with ethyl ether to obtain the title compound as a solid (4.9 g, 67%). MS (M+): 152.

Intermediate 15. tert-butyl [(1R,S)-2-(4-hydroxyphenyl)-1-methylethyl]carbamate To a solution of Intermediate 14 (4.9 g, 32.4 mmol) in dioxane (10 mL) was added potassium carbonate (9 g, 64.8 mmol) and a solution of di-tert-butyl dicarbonate (7.8 g, 35.6 mmol) in dioxane (10 mL). The reaction mixture was stirred at room temperature for 1 hour. The solvent was removed under reduced pressure and the crude was partitioned between ethyl acetate and water. The organic layer was washed with a solution of sodium hydrogen carbonate, ammonium chloride and brine. The solvent was removed under reduced pressure to obtain the title compound as oil (8.1 g, 95%) and used in the next step without further purification.

MS (M+): 252.

Intermediate 16. tert-butyl (2-{4[(1R,S)-2-(1-adamantyl)ethoxy]phenyl}-1-methylethyl)carbamate To a solution of Intermediate 15 (1 g, 4.3 mmol) in tetrahydrofuran (6 mL) and 1-Adamantaneethanol (0.77 g, 4.2 mmol) in tetrahydrofuran (6 mL) was added a solution of diethyl azodicarboxylate (2.9 mL, 6.4 mmol) and triphenylphosphine (1.6 g, 6.4 mmol) in tetrahydrofuran (4 mL). The reaction mixture was stirred at 80° C. for 48 hours. The solvent was removed under reduced pressure and partitioned between methylen chloride and water. The organic layer was washed with water, sodium hydrogen carbonate (4%) and brine. The solvent was removed under reduced pressure and the crude was purified by column chromatography with silica gel, eluting with hexane/ethyl acetate (30:1). The title compound was obtained as a solid (0.39 g, 22%). MS (M+): 414.

Intermediate 17. (1R,S)-1-{4-[2-(1-adamantyl)ethoxy]phenyl}propan-2-amine

A solution of Intermediate 16 (0.3 g, 0.75 mmol) in hydrogen chloride 1.25M in methanol was stirred at room temperature for 4 hours. The solvent was removed under reduced pressure and the title compound was obtained as a white solid (0.23 g, 97%) and used in the next step without further purification. MS (M+): 314.

Intermediate 18. 5-((1R)-2-[((1R,S)-2-{4-[2-(1-adamantyl)ethoxy]phenyl}-1-methylethyl)amino]-1-{[tert-butyl(dimethyl)silyl]oxy}ethyl)-8-(benzyloxy)-quinolin-2(1H)-one To a solution of Intermediate 17 (0.3 g, 0.93 mmol) and (R)-8-(benzyloxy)-5-(2-bromo-1-(tert-butyldimethylsilyloxy)ethyl)quinolin-2(1H)-one (0.44 g, 0.9 mmol) in dimethyl sulfoxide (4.5 mL) was added sodium iodide (0.2 g, 1.3 mmol) and sodium hydrogen carbonate (0.2 g, 2.7 mmol). The reaction mixture was heated under argon at 85° C. for 6 hours and poured into water. The organic layer was extracted with ethyl acetate and washed with water and ammonium chloride. The solvent was removed under reduced pressure and the crude was purified by column chromatography with silica gel, eluting with hexane/ethyl acetate (from 3:1 to 1:1). The title compound was obtained as a white foam (0.3 g, 35%). MS (M+): 722.

Intermediate 19. 5-{(1R)-2-[((1R,S)-2-{4-[2-(1-adamantyl)ethoxy]phenyl}-1-methylethyl)amino]-1-hydroxyethyl}-8-(benzyloxy)quinolin-2(1H)-one To a solution of Intermediate 18 (0.21 g, 0.3 mmol) in tetrahydrofuran (20 mL) was added tetrabutylammonium fluoride trihydrate (0.155 g, 0.59 mmol). The reaction mixture was stirred at room temperature for 6 hours and the solvent was removed under reduced pressure. The crude was partitioned between methylen chloride and water and the organic layer was washed several times with water. The solvent was removed under reduced pressure to obtain the title compound as a yellow oil (0.17 g, 95%), which was used in the next step without further purification. MS (M+): 607.

Example 2

5-{(1R)-2-[(2-{4-[2-(1-adamantyl)ethoxy]phenyl}-1-methylethyl)-amino]-1-hydroxyethyl}-8-hydroxyquinolin-2(1H)-one

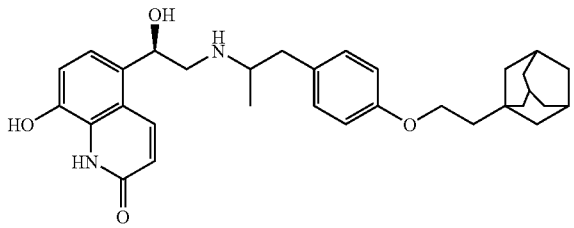

Obtained from Intermediate 19 (0.15 g, 0.25 mmol) and palladium on charcoal (10%, 0.03 g) by the same procedure described in Example 1 (reaction time: 48 hours). The crude was purified by column chromatography with silica gel, eluting with methylen chloride/methanol/ammonia (40:4:0.2) and the title compound was obtained as a yellow solid (0.056 g, 44%).

$^1$H-NMR (300 MHz, dimethylsulfoxide-D6): 0.88 (d, J=5.22 Hz, 3H); 1.55-1.57 (m, 8H); 1.60-1.64 (m, 5H); 1.90-1.93 (m, 3H); 2.39-2.77 (bs, 7H); 3.35 (bs, 3H); 3.90-3.96 (m, 2H); 4.96 (s, 1H); 6.5 (d, J=9.6 Hz, 1H); 6.75-7.05 (m, 6H); 8.15 (d, J=9.6 Hz, 1H).

MS (M+): 517.

Intermediate 20. tert-butyl [2-(4-hydroxyphenyl)ethyl]carbamate

To a solution of 4-(2-aminoethyl)phenol (2 g, 14.5 mmol) in a mixture of dioxane (12 mL) and water (30 mL) was added potassium carbonate (2 g, 14.8 mmol). To the mixture was slowly added a solution of di-tert-butyl dicarbonate (3.2 g, 14.6 mmol) in dioxane (15 mL) at 0° C. The reaction mixture was stirred at room temperature for 1.5 hours. The crude was partitioned between ethyl acetate and water and the organic layer was washed with water and sodium hydrogen carbonate (4%). The solvent was removed under reduced pressure and the title compound was obtained as an oil (3.4 g, 99%) and used in the next step without further purification. MS (M+): 238.

Intermediate 21. tert-butyl (2-{4-[2-(1-adamantyl)ethoxy]phenyl}ethyl)-carbamate Obtained from Intermediate 20 (0.12 g, 0.51 mmol), Intermediate 6 (0.2 g, 0.51 mmol) and cesium carbonate (0.165 g, 0.51 mmol) by the same procedure described in Intermediate 7 (reaction time: 24 h). The crude was purified by column chromatography with silica gel, eluting with hexane/ethyl acetate (10:1) to give the title compound (0.167 g, 80%) as colourless oil. MS (M+): 400.

Intermediate 22. (2-{4-[2-(1-adamantyl)ethoxy]phenyl}ethyl)amine

Obtained from Intermediate 21 (0.167 g, 1.42 mmol) in hydrogen chloride 1.25M in methanol by the same procedure described in Intermediate 17. The solvent was removed to give the title compound as a white solid salt (0.127 g, 98%), which was used in the next step without further purification. MS (M+): 300.

Intermediate 23. 5-((1R)-2-[(2-{4-[2-(1-adamantyl)ethoxy]phenyl}ethyl)amino]-1-{[tert-butyl(dimethyl)silyl]oxy}ethyl)-8-(benzyloxy)quinolin-2(1H)-one Obtained from Intermediate 22 (0.26 g, 0.87 mmol), (R)-8-(benzyloxy)-5-(2-bromo-1-(tert-butyldimethylsilyloxy)ethyl)quinolin-2(1H)-one (0.4 g, 0.82 mmol), sodium iodide (0.18 g, 1.2 mmol) and sodium hydrogen carbonate (0.2 g, 2.4 mmol) by the same procedure described in Intermediate 18. The precipitate obtained was collected by filtration and purified by column chromatography with silica gel, eluting with hexane/ethyl acetate (from 3:1 to 5:1) to give the title compound as a solid (0.157 g, 27%). MS (M+): 708.

Intermediate 24. 5-{(1R)-2-[(2-{4-[2-(1-adamantyl)ethoxy]phenyl}ethyl)amino]-1-hydroxyethyl}-8-(benzyloxy)quinolin-2(1H)-one Obtained from Intermediate 23 (0.15 g, 0.22 mmol) and tetrabutylammonium fluoride trihydrate (0.092 g, 0.35 mmol) by the same procedure described in Intermediate 19. The title compound was obtained as a white solid (0.1 g, 78%) and used in the next step without further purification. MS (M+): 593.

Example 3

5-{(1R)-2-[(2-{4-[2-(1-adamantyl)ethoxy]phenyl}ethyl)amino]-1-hydroxyethyl}-8-hydroxyquinolin-2(1H)-one

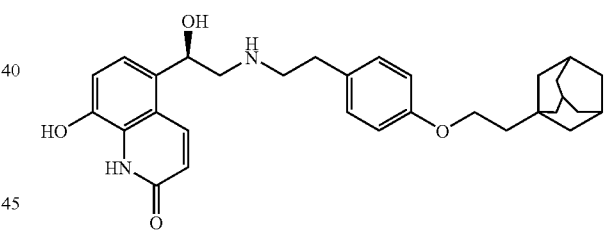

Obtained from Intermediate 24 (0.1 g, 0.17 mmol) and palladium on charcoal (10%, 0.02 g) by the same procedure described in Example 1 (reaction time: overnight). The crude obtained was triturated with ether giving the title compound as a white solid (0.081 g, 95%).

$^1$H-NMR (300 MHz, dimethylsulfoxide-D6): 1.48-1.7 (m, 14H); 1.93 (bs, 3H); 2.88-3.18 (m, 7H); 3.98 (t, J=7.1 Hz, 2H); 5.41 (s, 1H); 6.19 (bs, 1H); 6.58 (d, J=10.1 Hz, 1H); 6.89 (d, J=8.2 Hz, 1H); 7.0 (d, J=7.9 Hz, 1H); 7.11-7.17 (m, 3H); 8.2 (d, J=10.1 Hz, 1H); 10.53 (bs, 1H).

MS (M+): 503.

Intermediate 25. [5-((1R)-2-[(2-{4-[2-(1-adamantyl)ethoxy]phenyl}ethyl)-amino]-1-{[tert-butyl(dimethyl)silyl]oxy}ethyl)-2-(benzyloxy)phenyl]-formamide To a solution of Intermediate 22 (0.4 g, 1.34 mmol) and (R)—N-(2-(benzyloxy)-5-(2-bromo-1-(tert-butyldimethylsilyloxy)ethyl)phenyl)formamide (0.62 g, 0.82 mmol) in dimethyl sulfoxide (3 mL) was added sodium iodide (0.59 g, 3.99 mmol) and sodium hydrogen carbonate (0.67 g, 8.03 mmol). The reaction mixture was heated under argon at 130° C. for 1 hour. The mixture was poured into water and extracted with ether. The organic layer was washed with water and brine and the solvent was removed under reduced pressure. The title compound was obtained as yellow foam (0.84 g, 73%) and used in the next step without further purification. MS (M+): 684.

Intermediate 26. [5-{(1R)-2-[(2-{4-[2-(1-adamantyl) ethoxy]phenyl}ethyl)-amino]-1-hydroxyethyl}-2-(benzyloxy)phenyl]formamide To a solution of Intermediate 25 (1.23 g, 1.44 mmol) in tetrahydrofuran (20 mL) was added tetrabutylammonium fluoride on silica gel (1-1.5 mmol/g, 2 g). The reaction mixture was stirred first at room temperature overnight and then at 45° C. for 3 hours. Silica was filtrated and the solvent was removed under reduced pressure. The crude was dissolved in ethyl acetate and the organic layer was washed several times with water. The solvent was removed under reduced pressure and the crude was purified by column chromatography with silica gel, eluting with chloroform/methanol (75:1) to give the title compound as a solid (0.36 g, 61%). MS (M+): 569.

Example 4

(5-{(1R)-2-[(2-{4-[2-(1-adamantyl)ethoxy] phenyl}ethyl)amino]-1-hydroxyethyl}-2-hydroxyphenyl)formamide

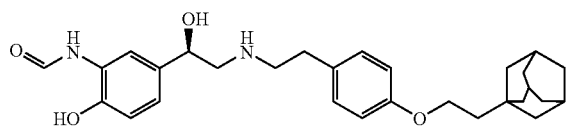

To a solution of Intermediate 26 (0.32 g, 0.56 mmol) in a mixture of methanol (5 mL) and tetrahydrofuran (5 mL) was added palladium on charcoal (10%, 0.03 g). The reaction mixture was hydrogenated at 40 psi for 3 days. The catalyst was filtered through Celite® and the solvent removed under reduced pressure. The crude was purified by chromatography eluting with chloroform/methanol (6:1) to give the title compound as a solid (0.102 g, 37%)
$^1$H-NMR (300 MHz, dimethylsulfoxide-D6): 1.48-1.7 (m, 16H); 1.92 (bs, 3H); 2.60-2.64 (m, 4H); 2.75 (bs, 2H); 3.97 (t, J=7.14 Hz, 2H); 4.5 (s, 1H); 6.80-6.83 (m, 4H); 7.08 (d, J=8.2 Hz, 2H); 8.03 (s, 1H); 8.26 (s, 1H); 9.56 (s, 1H).
MS (M+): 479.

Intermediate 27. 2-[((2R,S)-2-{4-[2-(1-adamantyl) ethoxy]phenyl}ethyl)amino]-1-[4-(benzyloxy)-3-(hydroxymethyl)phenyl]ethanol A solution of Intermediate 22 (0.32 g, 1.1 mmol) and 1-(4-(benzyloxy)-3-(hydroxymethyl)phenyl)-2,2-dihydroxyethanone (0.32 g, 1.13 mmol) in a mixture of tetrahydrofuran (5 mL) and methanol (5 mL) was stirred at room temperature for 4 hours. The reaction mixture was cooled at 0° C. and sodium borohydride (0.12 g, 3.2 mmol) was added. The resulting mixture was stirred at room temperature overnight. The crude was partitioned between ethyl acetate and water and the organic layer was washed with water and sodium hydrogen carbonate (4%). The solvent was removed under reduced pressure and the crude obtained was purified by column chromatography with silica gel, eluting by chloroform/methanol (from 75:1 to 25:1) to give the title compound as oil (0.158 g, 25%). MS (M+): 556.

Example 5

4-{2-[(2-{4-[2-(1-adamantyl)ethoxy]phenyl}ethyl) amino]-1-hydroxyethyl}-2-(hydroxymethyl)phenol

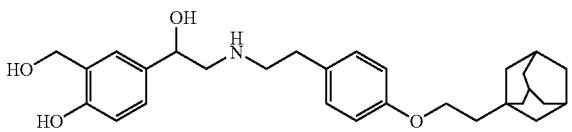

To a solution of Intermediate 27 (0.158 g, 0.26 mmol) in methanol (16 mL) was added palladium on charcoal (10%, 0.03 g). The reaction mixture was hydrogenated under a balloon pressure for 24 hours. The catalyst was filtered through Celite® and the solvent removed under reduced pressure. The title compound was obtained as a fumarate (0.077 g, 62%).
$^1$H-NMR (300 MHz, dimethylsulfoxide-D6): 1.48-1.7 (m, 14H); 1.93 (bs, 3H); 2.80-2.99 (m, 6H); 3.98 (t, J=6.59 Hz, 2H); 4.47 (s, 2H); 4.72 (d, J=7.9 Hz, 1H); 6.49 (s, 1H); 6.73 (d, J=8.24 Hz, 1H); 6.85 (d, J=8.24 Hz, 1H); 7.03 (d, J=7.96 Hz, 1H); 7.12 (d, J=7.96 Hz, 1H); 7.3 (s, 1H, fumaric). MS (M+): 466.

Intermediate 28. 3-(2-aminoethyl)phenol

A solution of 2-(3-methoxyphenyl)ethanamine (10 g, 66.1 mmol) in aqueous bromhydric acid (48%, 67 mL) was stirred at 140° C. for 4 hours. The solvent was removed under reduced pressure and the crude was washed with a mixture of methylen chloride and hexane (1:1). The title compound was obtained as a grey oil and was used in the next step without further purification. MS (M+): 138.

Intermediate 29. tert-butyl [2-(3-hydroxyphenyl)ethyl]carbamate

Obtained from Intermediate 28 (11 g, 80.2 mmol), potassium carbonate (23.1 g) and di-tert-butyl dicarbonate (11.2 g, 51.3 mmol) by the same procedure described in Intermediate 20. The title compound was obtained as a solid (10.8 g) and used in the next step without further purification. MS (M+): 238.

Intermediate 30. tert-butyl (2-{3-[2-(1-adamantyl) ethoxy]phenyl}ethyl)-carbamate To a solution of Intermediate 29 (10 g, 2.37 mol) in dimethylformamide (75 mL) was slowly added sodium hydride (60%, 1.18 g). The mixture was stirred at room temperature for 30 minutes. A solution of Intermediate 44 (5.9 g, 22.8 mmol) in dimethylformamide (25 mL) was added into the previous mixture. The reaction was stirred at 60° C. overnight. The solvent was removed under reduced pressure and the crude was partitioned between ethyl acetate and water. The solvent was removed under reduced pressure to give the title compound as a solid, which was used in the next step without further purification. MS (M+): 400.

Intermediate 31. (2-{3-[2-(1-adamantyl)ethoxy]phenyl}ethyl)amine

To a solution of Intermediate 30 (7 g, 17.5 mmol) in dioxane (70 mL) was added hydrogen chloride (1.25M in dioxane, 25 mL). The reaction mixture was stirred at room temperature overnight. The precipitate was filtrated and washed with dioxane and ether. The crude was purified by column chromatography with silica gel, eluting with methylen chloride/methanol/ammonium (40:4:0.2) and the title compound was obtained as an oil (2.6 g, 50%). (M+): 300.

Intermediate 32. 5-((1R)-2-[(2-{3-[2-(1-adamantyl)ethoxy]phenyl}ethyl)amino]-1-{[tert-butyl(dimethyl)silyl]oxy}ethyl)-8-(benzyloxy)quinolin-2(1H)-one To a solution of Intermediate 31 (0.51 g, 1.7 mmol) in dimethyl sulfoxide (1.5 mL) and (R)-8-(benzyloxy)-5-(2-bromo-1-(tert-butyldimethylsilyloxy)ethyl)quinolin-2(1H)-one (1.06 g, 2.17 mmol) in dimethyl sulfoxide (2 mL) was added sodium hydrogen carbonate (0.53 g, 6.37 mmol) and sodium iodide (0.970 g, 6.47 mmol). The reaction mixture was stirred at 120° C. for 2 hours. The reaction was poured into water and filtered. The crude was purified by column chromatography with silica gel, eluting by methylen chloride giving the title compound as a solid (0.84 g, 63%). MS (M+): 708.

Intermediate 33. 5-{(1R)-2-[(2-{3-[2-(1-adamantyl)ethoxy]phenyl}ethyl)-amino]-1-hydroxyethyl}-8-(benzyloxy)quinolin-2(1H)-one To a solution of Intermediate 32 (0.48 g, 0.68 mmol) in tetrahydrofuran (12 mL) was added tetrabutylammonium fluoride trihydrate (0.284 g, 1.09 mmol). The reaction mixture was stirred at 45° C. for 3.5 hours. The solvent was removed under reduced pressure and the crude was partitioned between ethyl acetate and water. The organic layer was washed several times with water and the solvent was removed under reduced pressure to give the title compound as a yellow solid (0.375 g, 88%). MS (M+): 593.

Example 6

5-{(1R)-2-[(2-{3-[2-(1-adamantyl)ethoxy]phenyl}ethyl)amino]-1-hydroxyethyl}-8-hydroxyquinolin-2(1H)-one

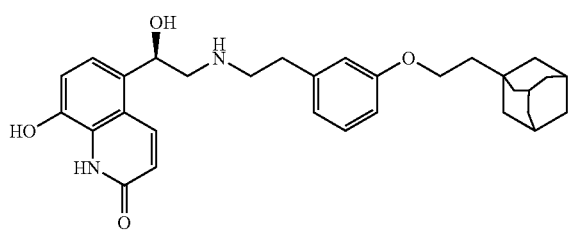

Obtained from Intermediate 33 (0.365 g, 0.62 mmol) and palladium on charcoal (10%, 0.075 g) by the same procedure described in Example 1 (reaction time: 20 hours). The crude was purified by column chromatography with silica gel, eluting with methylen chloride/methanol/ammonium (40:2.5:0.1) and the title compound was obtained as a solid (0.113 g, 65%).

$^1$H-NMR (300 MHz, dimethylsulfoxide-D6): 1.57-1.73 (m, 14H); 1.96 (bs, 3H); 2.84 (bs, 6H); 2.94 (t, J=6.5 Hz, 2H); 4.00 (t, J=7.14 Hz, 2H); 5.11 (bs, 1H); 6.50 (d, J=9.69 Hz, 1H); 6.75 (m, 3H); 6.83 (d, J=8.0 Hz, 1H); 7.07 (d, J=7.96 Hz, 1H); 7.19 (d, J=7.45 Hz, 1H); 8.06 (d, J=8.69 Hz, 1H).
MS (M+): 503.

Intermediate 34. 1-adamantylmethyl trifluoromethanesulfonate

To a solution of 1-adamantanmethanol (5 g, 30.07 mmol) in methylen chloride (23 mL) and ethyldiisopropyl amine (5.76 mL, 33.07 mmol) was added at −50° C. a solution of trifluoromethansulfonic anhydride (5.55 mL, 33.05 mmol) in methylen chloride (5 mL). The resulting reaction mixture was stirred at room temperature overnight. The solvent was removed under reduced pressure and the crude was purified by column chromatography with silica gel, eluting with hexane/ethyl acetate (20:5). The title compound was obtained as colourless oil (5.5 g, 61%).
$^1$H-NMR (300 MHz, CDCl3): 4.09 (s, 2H); 2.05 (bs, 3H); 1.59-1.78 (m, 12H).

Intermediate 35. tert-butyl {2-[4-(1-adamantylmethoxy)phenyl]ethyl}-carbamate To a solution of Intermediate 34 (4.2 g, 14.07 mmol) in anhydrous dimethylformamide (12 mL) and a solution of Intermediate 20 (0.98 g, 4.14 mmol) in anhydrous dimethylformamide (2 mL) was added cesium carbonate (1.8 g, 5.62 mmol). The reaction mixture was stirred at 65° C. for 72 hours. The crude was poured into water and extracted with ether. The organic layer was washed with a solution of sodium hydroxide 2N, water and brine. The solvent was removed under reduced pressure and the title compound was obtained as an oil (1.3 g, 67%) and used in the next step without further purification. MS (M+): 386.

Intermediate 36. {2-[4-(1-adamantylmethoxy)phenyl]ethyl}amine

Obtained from Intermediate 35 (1.3 g, 3.37 mmol) in hydrogen chloride 1.25M in methanol by the same procedure described in Intermediate 17. The precipitate obtained was separated by filtration giving the title compound as a yellow solid (0.84 g, 87%). MS (M+): 286.

Intermediate 37. 5-((1R)-2-({2-[4-(1-adamantylmethoxy)phenyl]ethyl}amino)-1-{[tert-butyl(dimethyl)silyl]oxy}ethyl)-8-(benzyloxy)quinolin-2(1H)-one Obtained from Intermediate 36 (0.162 g, 0.57 mmol), (R)-8-(benzyloxy)-5-(2-bromo-1-(tert-butyldimethylsilyloxy)ethyl)quinolin-2(1H)-one (0.205 g, 0.42 mmol), sodium hydrogen carbonate (0.216 g, 2.57 mmol) and sodium iodide (0.184 g, 1.23 mmol) by the same procedure described in Intermediate 32 (reaction time: 3 hours). The crude was purified by column chromatography with silica gel, eluting with hexane/ethyl acetate (from 3:1 to 1:1) and the title compound was obtained as a solid (0.104 g, 32%). MS (M+): 694.

Intermediate 38. 5-[(1R)-2-({2-[4-(1-adamantylmethoxy)phenyl]ethyl}amino)-1-hydroxyethyl]-8-(benzyloxy)quinolin-2(1H)-one Obtained from Intermediate 37 (0.243 mg, 0.35 mmol) in tetrahydrofuran (3 mL) and tetrabutylammonium fluoride trihydrate (0.16 g, 0.61 mmol) by the same procedure described in Intermediate 33. A treatment with hexane gave the desired compound as a yellow solid (0.17 g, 80%). MS (M+): 579.

Example 7

5-[(1R)-2-({2-[4-(1-adamantylmethoxy)phenyl]ethyl}amino)-1-hydroxyethyl]-8-hydroxyquinolin-2(1H)-one

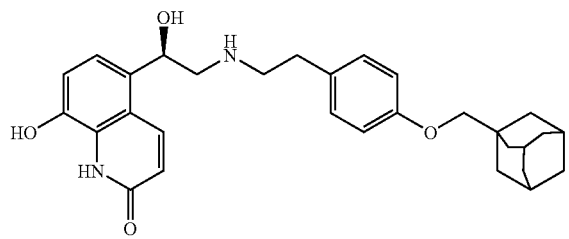

Obtained from Intermediate 38 (0.17 g, 0.32 mmol) and palladium on charcoal (10%, 0.034 g) by the same procedure described in Example 1 (reaction time: 2 days). The crude obtained was triturated with ether and filtrated to obtain the title compound as a yellow solid (0.102 g, 69%).

$^1$H-NMR (300 MHz, dimethylsulfoxide-D6): 1.66-1.79 (m, 12H); 2.02 (bs, 3H); 2.99 (bs, 2H); 3.19 (bs, 2H); 3.54 (bs, 2H); 5.4 (bs, 1H); 6.61 (d, J=9.89 Hz, 1H); 6.93 (d, J=8.51 Hz, 2H); 7.05 (d, J=8.24 Hz, 1H); 7.19-7.21 (m, 3H); 8.29 (d, J=9.89 Hz, 1H); 10.57 (d, J=10.4 Hz, 1H).

MS (M+): 489.

Intermediate 39.
3-(1-adamantylmethoxy)benzaldehyde

To a solution of 3-hydroxybenzaldehyde (0.54 g, 4.42 mmol) in dimethyl sulfoxide (5 mL) was added sodium hydride (60%, 0.186 g) in portions. The mixture was stirred for 10 minutes and then was added a solution of Intermediate 34 (1.32 g, 4.42 mmol) in dimethyl sulfoxide (2 mL). The reaction mixture was stirred at 70° C. for 48 hours and the mixture was poured into water and extracted with ether. The organic layer was washed with a solution of sodium hydroxide 2N, water and brine. The solvent was removed under reduced pressure and the crude was purified by column chromatography with silica gel, eluting by hexane/ethyl acetate (10:1) to give the title compound as an oil (0.493 g, 41%).

Intermediate 40. 1-adamantylmethyl 3-[(E)-2-nitrovinyl]phenyl ether

Obtained from Intermediate 39 (0.49 g, 1.81 mmol), ammonium acetate (0.1 g, 1.3 mmol) and nitromethane (0.213 g, 3.48 mmol) by the same procedure described in Intermediate 1 (reaction time: 36 hours). The title compound was obtained (0.54 g, 58%) and used in the next step without further purification. MS (M+): 314.

Intermediate 41. {2-[3-(1-adamantylmethoxy)phenyl]ethyl}amine

Obtained from Intermediate 40 (0.165 g, 0.53 mmol) and lithium aluminium hydride (0.066 g, 1.74 mmol) by the same procedure described in Intermediate 3 (reaction time: 3 hours). The crude was purified by column chromatography with silica gel, eluting with chloroform to give the title compound as a white solid (0.174 g, 50%). MS (M+): 286.

Intermediate 42. 5-((1R)-2-({2-[3-(1-adamantylmethoxy)phenyl]ethyl}amino)-1-{[tert-butyl(dimethyl)silyl]oxy}ethyl)-8-(benzyloxy)quinolin-2(1H)-one To a solution of Intermediate 41 (0.117 g, 0.41 mmol) in dimethyl sulfoxide (0.8 mL) and a solution of (R)-8-(benzyloxy)-5-(2-bromo-1-(tert-butyldimethylsilyloxy)-ethyl)quinolin-2(1H)-one (0.2 g, 0.41 mmol) in dimethyl sulfoxide (0.8 mL) was added sodium hydrogen carbonate (0.103 g, 1.23 mmol) and sodium iodide (0.092 g, 0.61 mmol). The resulting reaction mixture was stirred at 150° C. for 1 hour. The mixture was poured into water and the precipitate was collected by filtration and washed with ether and ethyl acetate. The title compound was obtained as a brown solid (0.231 g, 57%) and was used in the next step without further purification. MS (M+): 694.

Intermediate 43. 5-[(1R)-2-({2-[3-(1-adamantylmethoxy)phenyl]ethyl}amino)-1-hydroxyethyl]-8-(benzyloxy)quinolin-2(1H)-one Obtained from a solution of Intermediate 42 (0.231 g, 0.33 mmol) in tetrahydrofuran (10 mL) and tetrabutylammonium fluoride trihydrate (0.177 g, 0.56 mmol) by the same procedure described in Intermediate 33. The crude was purified by column chromatography with silica gel, eluting with methylen chloride/methanol/ammonium (40:2.5:0.1) to give the title compound as a solid (0.075 g, 39%). MS (M+): 579.

Example 8

5-[(1R)-2-({2-[3-(1-adamantylmethoxy)phenyl]ethyl}amino)-1-hydroxyethyl]-8-hydroxyquinolin-2(1H)-one

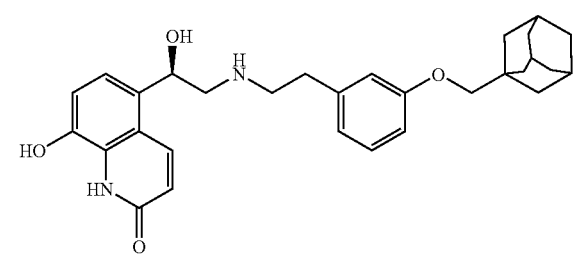

To a solution of Intermediate 43 (0.075 g, 0.13 mmol) in a mixture of methanol (3 mL) and tetrahydrofuran (1 mL) was added some drops of hydrogen chloride 1.25M in methanol and palladium on charcoal (10%, 0.015 g). The reaction mixture was hydrogenated under a balloon pressure overnight. The catalyst was filtered through Celite® and the solvent removed under reduced pressure. The crude was treated with ether and collected by filtration to obtain the title compound as a yellow solid (0.055 g, 82%).

$^1$H-NMR (300 MHz, dimethylsulfoxide-D6): 1.62-1.75 (m, 12H); 1.98 (bs, 3H); 2.93-3.20 (m, 4H); 3.51 (s, 2H); 5.42 (bs, 1H); 6.57 (d, J=9.89 Hz, 1H); 6.80-6.82 (m, 3H); 7.00 (d, J=8.24 Hz, 1H); 7.16 (d, J=8.24 Hz, 1H); 7.22 (t, J=7.96 Hz, 1H); 8.23 (d, J=9.89 Hz, 1H); 10.5 (s, 1H).

MS (M+): 489.

Intermediate 44. 2-(1-adamantyl)ethyl methanesulfonate

A solution of 1-adamantylethanol (3 g, 16.64 mmol) in methylen chloride (50 mL) and triethylamine (2.8 mL, 19.95 mmol) was stirred for 10 minutes. Then methanesulfonyl chloride (1.55 mL, 20.03 mmol) was added and the resulting reaction mixture was stirred at room temperature for 72 hours. The crude was partitioned between methylen chloride and a solution of sodium hydrogen carbonate (4%). The organic layer was washed with water and brine and the solvent was removed under reduced pressure to give the title compound as a yellow oil (4.1 g, 96%), which was used in the next step without further purification.

Intermediate 45. 3-(1-adamantyl)propanenitrile

To a solution of Intermediate 44 (4.1 g, 16.01 mmol) in dimethyl sulfoxide (18 mL) was slowly added sodium cyanide (0.98 g, 20 mmol). The reaction mixture was stirred at 100° C. for 1.5 hours and at room temperature overnight. The crude was partitioned between ether and water and the organic layer was washed with water. The solvent was removed under reduced pressure and the title compound was obtained as a colourless solid (2.9 g, 98%) and used in the next step without further purification.

Intermediate 46. 3-(1-adamantyl)propanoic acid

To a solution of Intermediate 45 (2.9 g, 15.76 mmol) in ethanol (20 mL) was added under nitrogen potassium hydroxide (6.2 g, 110.5 mmol). The reaction mixture was refluxed for 3 hours and stirred at room temperature overnight. The solvent was removed under reduced pressure and the crude was partitioned between water and ether. The aqueous layer was washed twice with ether and then acidified with hydrochloric acid 2N. The precipitate was collected by filtration to obtain the title compound as a yellow solid (2.9 g, 88%).

Intermediate 47. methyl 3-(1-adamantyl)propanoate

To a solution of Intermediate 46 (2.9 g, 13.98 mmol) in methanol (22.6 mL) was added dropwise sulphuric acid (0.4 mL, 6.94 mmol) during 15 minutes at 0° C. The resulting reaction mixture was refluxed for 2 hours. The solvent was removed under reduced pressure and the crude was partitioned between ethyl acetate and water. The organic layer was washed with a solution of sodium hydrogen carbonate (4%), water and brine. The solvent was removed under reduced pressure and the title compound was obtained as a red oil (2.9 g, 95%) and was used in the next step without further purification.

Intermediate 48. 3-(1-adamantyl)propan-1-ol

A solution of Intermediate 47 (3.89 g, 17.49 mmol) in anhydrous tetrahydrofuran (5 mL) was slowly added under argon at 0° C. to a solution of lithium aluminium hydride (0.74 g, 19.5 mmol) in tetrahydrofuran (22 mL). The resulting mixture was stirred at room temperature for 5 hours. Then water (20 mL), sodium hydroxide 4N (20 mL) and finally water again (40 mL) were added into the solution at 0° C. The mixture was stirred for some minutes and the resulting salts were filtered through a pad of Celite®. The solvent was removed under reduced pressure and the title compound was obtained as a colourless solid (3.3 g, 97%) and used in the next step without further purification.

Intermediate 49. 3-(1-adamantyl)propyl methanesulfonate

Obtained from Intermediate 48 (2.28 g, 11.73 mmol) in methylen chloride (40 mL), triethylamine (4 mL, 27.9 mmol) and methanesulfonyl chloride (2.18 mL, 28.1 mmol) by the same procedure described for Intermediate 44. The crude obtained was partitioned between methylen chloride and water and the organic layer was washed with a solution of sodium hydrogen carbonate (4%), water and brine. The solvent was removed under reduced pressure and the title compound was obtained as a colourless oil (2.4 g, 99%) and used in the next step without further purification.

Intermediate 50. tert-butyl (2-{4-[3-(1-adamantyl)propoxy]phenyl}ethyl)-carbamate Obtained from Intermediate 20 (0.62 g, 2.60 mmol), Intermediate 49 (0.92 g, 3.39 mmol) and cesium carbonate (1.1 g, 3.38 mmol) by the same procedure described in Intermediate 7. The solvent was removed under reduced pressure to give the title compound (1.21 g, 79%), which was used in the next step without further purification.

Intermediate 51. 2-{4-[3-(1-adamantyl)propoxy]phenyl}ethanamine

Obtained from Intermediate 50 (1.2 g, 2.94 mmol) in hydrogen chloride 1.25 M in methanol by the same procedure described in Intermediate 17. The solvent was removed under reduced pressure and the title compound was obtained as a salt (0.62 g, 67%), which was used in the next step without further purification. MS (M+): 314.

Intermediate 52. 5-((1R)-2-[(2-{4-[3-(1-adamantyl)propoxy]phenyl}ethyl)-amino]-1-{[tert-butyl(dimethyl)silyl]oxy}ethyl)-8-(benzyloxy)quinolin-2(1H)-one Obtained from Intermediate 51 (0.62 g, 1.97 mmol), (R)-8-(benzyloxy)-5-(2-bromo-1-(tert-butyldimethylsilyloxy)ethyl)quinolin-2(1H)-one (0.96 g, 1.97 mmol), sodium iodide (0.06 g, 0.4 mmol) and sodium hydrogen carbonate (0.33 g, 3.94 mmol) by the same procedure described in Intermediate 32 (reaction time: 1.5 hours). The crude was purified by column chromatography with silica gel, eluting by methylen chloride/methanol (from 90:1 to 90:1) and the title compound was obtained as a solid (0.6 g, 35%). MS (M+): 722.

Intermediate 53. 5-{(1R)-2-[(2-{4-[3-(1-adamantyl)propoxy]phenyl}ethyl)-amino]-1-hydroxyethyl}-8-(benzyloxy)quinolin-2(1H)-one Obtained from Intermediate 52 (0.6 g, 0.84 mmol) and tetrabutylammonium fluoride trihydrate (0.45 g, 1.44 mmol) by the same procedure described in Intermediate 19. The crude was purified by column chromatography with silica gel, eluting by methylen chloride/methanol (90:6) to give the title compound as a solid (0.4 g, 78%). MS (M+): 607

Example 9

5-{(1R)-2-[(2-{3-[3-(1-adamantyl)propoxy]phenyl}ethyl)amino]-1-hydroxyethyl}-8-hydroxyquinolin-2(1H)-one

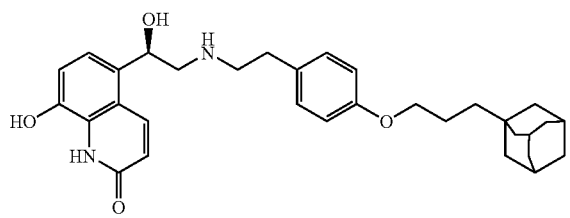

Obtained from Intermediate 53 (0.33 mg, 0.55 mmol) and palladium on charcoal (10%, 0.04 g) by the same procedure described in Example 1 (reaction time: 2 days). The crude obtained was triturated with ether and methylen chloride to give the title compound as a yellow solid (0.21 g, 74%).

$^1$H-NMR (300 MHz, dimethylsulfoxide-D6): 1.10-1.17 (m, 2H); 1.46 (bs, 6H); 1.64 (bs, 8H); 1.92 (bs, 3H); 2.9-3.18 (m, 4H); 3.89 (t, J=6.6 Hz, 3H); 5.4 (bs, 1H); 6.18 (bs, 1H); 6.57 (d, J=9.9 Hz, 1H); 6.87 (d, J=8.24 Hz, 2H); 7.00 (d, J=8.24 Hz, 1H); 7.15 (dd, J=8.24, 5.77 Hz, 3H); 8.22 (d, J=9.89 Hz, 1H); 10.5 (bs, 1H).

MS (M+): 407.

Intermediate 54. tert-butyl {2-[3-(benzyloxy)phenyl]ethyl}carbamate

To a solution of 2-(3-(benzyloxy)phenylethanamine (2.87 g, 12.63 mmol) in dioxane (110 mL) was added a solution of sodium hydroxide (0.5 g, 12.65 mmol) in water (5 mL) at 5° C. Then a solution of di-tert-butyldicarbonate (2.76 g, 12.65 mmol) in dioxane (20 mL) was added dropwise. The reaction mixture was stirred at 5° C. for 1 hour and at room temperature overnight. The solvent was removed under reduced pressure and the crude was partitioned between ethyl acetate and water. The organic layer was washed with water and the crude was purified by column chromatography with silica gel, eluting by hexane/ethyl acetate (15:1) to give the title compound as solid (1.43 g, 34%). MS (M+): 328.

Intermediate 55. tert-butyl [2-(3-hydroxyphenyl)ethyl]carbamate

To a solution of Intermediate 54 (1.4 g, 4.37 mmol) in methanol (50 mL) was added palladium on charcoal (10%, 0.143 g). The reaction mixture was hydrogenated under a balloon pressure at room temperature overnight. The catalyst was filtered through Celite® and the solvent removed under reduced pressure to give the title compound as a solid, which was used in the next step without further purification. MS (M+): 238.

Intermediate 56. tert-butyl (2-{3-[3-(1-adamantyl)propoxy]phenyl}ethyl-carbamate Obtained from Intermediate 55 (0.94 g, 3.97 mmol), Intermediate 49 (1.4 g, 5.18 mmol) and cesium carbonate (1.6 g, 5.16 mmol) by the same procedure described in Intermediate 7 (reaction time: overnight). The solvent was removed under reduced pressure to give the title compound as a solid (1.8 g, 98%), which was used in the next step without further purification. MS (M+): 414.

Intermediate 57. 2-{3-[3-(1-adamantyl)propoxy]phenyl}ethanamine

Obtained from Intermediate 56 (1.8 g, 4.38 mmol) in hydrogen chloride 1.25M in methanol by the same procedure described in Intermediate 17. The solvent was removed under reduced pressure and the title compound was obtained as a salt (1 g, 68%), which was used in the next step without further purification. MS (M+): 314.

Intermediate 58. 5-((1R)-2-[(2-{3-[3-(1-adamantyl)propoxy]phenyl}ethyl)-amino]-1-{[tert-butyl(dimethyl)silyl]oxy}ethyl)-8-(benzyloxy)quinolin-2(1H)-one Obtained from Intermediate 57 (0.64 g, 2.04 mmol), (R)-8-(benzyloxy)-5-(2-bromo-1-(tert-butyldimethylsilyloxy)ethyl)quinolin-2(1H)-one (0.99 g, 2.04 mmol), sodium hydrogen carbonate (0.34 g, 4.07 mmol) and sodium iodide (0.06 g, 0.41 mmol) by the same procedure described in Intermediate 32 (reaction time: 1 hour). The crude was purified by column chromatography with silica gel, eluting by methylen chloride/methanol (from 90:1 to 90:2) and the title compound was obtained as a white solid (0.48 g, 33%). MS (M+): 722.

Intermediate 59. 5-{(1R)-2-[(2-{3-[3-(1-adamantyl)propoxy]phenyl}ethyl)-amino]-1-hydroxyethyl}-8-(benzyloxy)quinolin-2(1H)-one Obtained from Intermediate 58 (0.48 g, 0.67 mmol) in tetrahydrofuran (10 mL) and tetrabutylammonium fluoride trihydrate (0.36 g, 1.13 mmol) by the same procedure described in Intermediate 19. The crude was purified by column chromatography with silica gel, eluting by methylen chloride/methanol (90:4) and the title compound was obtained as a solid (0.25 g, 62%). MS (M+): 607.

Example 10

5-{(1R)-2-[(2-{4-[3-(1-adamantyl)propoxy]phenyl}ethyl)amino]-1-hydroxyethyl}-8-hydroxyquinolin-2(1H)-one

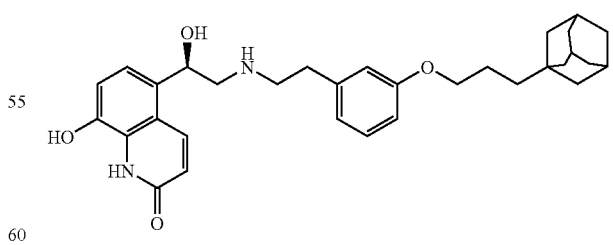

Obtained from Intermediate 59 (0.25 g, 0.42 mmol) and palladium on charcoal (10%, 0.025 g) by the same procedure described in Example 1 (reaction time: 3 days). The crude was purified by column chromatography with silica gel, eluting with methylen chloride/methanol (from 30:1 to 10:1) to give the title compound as a solid (0.031 g, 20%).

¹H-NMR (300 MHz, dimethylsulfoxide-D6): 1.16-1.24 (m, 2H); 1.47 (bs, 6H); 1.64 (bs, 8H); 2.51 (bs, 3H); 2.85-3.1 (m, 6H); 3.90 (t, J=6.32 Hz, 2H); 5.31 (bs, 1H); 6.56 (d, J=9.89 Hz, 1H); 6.79 (bs, 3H); 6.98 (d, J=8.24 Hz, 1H); 7.13 (d, J=8.24 Hz, 1H); 7.21 (t, J=8.52 Hz, 1H); 8.2 (d, J=9.88 Hz, 1H).

MS (M+): 407.

Intermediate 60. [5-((1R)-2-[(2-{3-[2-(1-adamantyl) ethoxy]phenyl}ethyl-)amino]-1-{[tert-butyl(dimethyl)silyl]oxy}ethyl)-2-(benzyloxy)phenyl] formamide Obtained from Intermediate 31 (0.9 g, 3.01 mmol), (R)—N-(2-(benzyloxy)-5-(2-bromo-1-(tert-butyldimethylsilyloxy)ethyl)phenyl)formamide (1.4 g, 3.01 mmol), sodium iodide (0.5 g, 3 mmol) and sodium hydrogen carbonate (0.8 g, 9.05 mmol) by the same procedure described in Intermediate 25 (reaction time: 40 minutes). The crude obtained was purified by column chromatography with silica gel, eluting with methylen chloride/methylen chloride:methanol (1:3) and the title compound was obtained as a foam (1.03 g, 50%).

Intermediate 61. [5-{(1R)-2-[(2-{3-[2-(1-adamantyl) ethoxy]phenyl}ethyl)-amino]-1-hydroxyethyl}-2-(benzyloxy)phenyl]formamide Obtained from Intermediate 60 (1 g, 1.46 mmol) and tetrabutyl ammonium fluoride trihydrate (0.69 g, 2.64 mmol) by the same procedure described in Intermediate 33. The crude obtained was purified by column chromatography with silica gel, eluting with methylen chloride/methylen chloride:methanol (99:1) to give the title compound as an oil (0.8 g, 96%).

Example 11

(5-{(1R)-2-[(2-{3-[2-(1-adamantyl)ethoxy] phenyl}ethyl)amino]-1-hydroxyethyl}-2-hydroxyphenyl)formamide

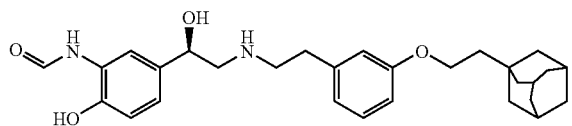

Obtained from Intermediate 61 (0.8 g, 1.41 mmol) and palladium on charcoal (10%, 0.15 g) by the same procedure described in Example 1 (reaction time: 3 hours). The crude was purified by column chromatography with silica gel, eluting with methylen chloride/methanol (from 98:2 to 9:1) and the title compound was obtained as a solid (0.32 g, 47%).

¹H-NMR (300 MHz, CDCl3): 1.51-1.64 (m, 14H); 1.92 (bs, 3H); 2.64-2.80 (m, 6H); 3.97 (bs, 2H); 4.5 (bs, 1H); 6.74-6.85 (m, 5H); 7.15 (bs, 1H); 8.02 (s, 1H); 8.25 (s, 1H); 9.54 (s, 1H).

MS (M+): 479.

Intermediate 62. 3-(2R,S)-2-aminopropyl)phenol

Obtained from Intermediate 3 (15.2 g, 62.9 mmol) and palladium on charcoal (10%, 1.4 g) by the same procedure described in Intermediate 5. The crude obtained was crystallized giving the title compound as a solid (9.5 g, 99%). MS (M+): 152.

Intermediate 63. 3-[(2R)-2-aminopropyl]phenol

Obtained from Intermediate 62 (9.5 g, 62.9 mmol) and D-tartaric acid (9.4 g, 62.6 mmol) by the same procedure described in Journal of Medicinal Chemistry (5276) 2002, Vol. 45, No. 24. The title compound was obtained as a solid (2.1 g, 44%). [□]D=–13.7° [c=1.17, MeOH].

Intermediate 64. tert-butyl [(1R)-2-(3-hydroxyphenyl)-1-methylethyl]-carbamate

Obtained from Intermediate 63 (2.1 g, 13.9 mmol), di-tert-butyl dicarbonate (3.08 g, 13.7 mmol) and potassium carbonate (3.2 g, 23.1 mmol) by the same procedure described in Intermediate 20. The title compound was obtained as a solid (3.5 g, 99.9%) and used in the next step without further purification. MS (M+): 252.

Intermediate 65. tert-butyl ((1R)-2-{3-[2-(1-adamantyl)ethoxy]phenyl}-1-methylethyl)carbamate Obtained from Intermediate 64 (3.5 g, 13.8 mmol), Intermediate 44 (3.5 g, 13.5 mmol) and sodium hydride (60%, 0.5 g) by the same procedure described in Intermediate 30. The title compound was obtained as a solid (5.8 g, 99.9%) and used in the next step without further purification. MS (M+): 414.

Intermediate 66. ((1R)-2-{3-[2-(1-adamantyl)ethoxy] phenyl}-1-methylethyl)-amine Obtained from Intermediate 65 (5.8 g, 14 mmol) and hydrogen chloride (4M in dioxane, 20 mL) by the same procedure described in Intermediate 8. The crude obtained was purified by column chromatography with silica gel, eluting with methylen chloride/methanol/ammonium (40:4:0.2) and the title compound was obtained (2.5 g, 58%). MS (M+): 314.

Intermediate 67. [5-((1R)-2-[((1R)-2-{3-[2-(1-adamantyl)ethoxy]phenyl}-1-methylethyl)amino]-1-{[tert-butyl(dimethyl)silyl]oxy}ethyl)-2-(benzyloxy)-phenyl]formamide Obtained from Intermediate 66 (0.3 g, 0.96 mmol), (R)—N-(2-(benzyloxy)-5-(2-bromo-1-(tert-butyldimethylsilyloxy)ethyl)phenyl)formamide (0.45 g, 0.97 mmol), sodium iodide (0.4 g, 2.94 mmol) and sodium hydrogen carbonate (0.2 g, 2.86 mmol) by the same procedure described in Intermediate 25 (reaction time: 50 minutes). The crude obtained was purified by column chromatography with silica gel, eluting with methylen chloride/methanol (from 1:99 to 2:99) to give the title compound as an oil (0.3 g, 45%). MS (M+): 698.

Intermediate 68. [5-{(1R)-2-[((1R)-2-{3-[2-(1-adamantyl)ethoxy]phenyl}-1-methylethyl)amino]-1-hydroxyethyl}-2-(benzyloxy)phenyl]formamide Obtained from Intermediate 67 (0.3 g, 0.43 mmol) and tetrabutylammonium fluoride trihydrate (0.24 g, 0.92 mmol) by the same procedure described in Intermediate 33. The crude obtained was purified by column chromatography with silica gel, eluting with methylen chloride/methanol (from 98:2 to 95:5) to give the title compound as an oil (0.24 g, 95%). MS (M+): 583.

Example 12

(5-{(1R)-2-[((1R)-2-{3-[2-(1-adamantyl)ethoxy]phenyl}-1-methylethyl)amino]-1-hydroxyethyl}-2-hydroxyphenyl)formamide

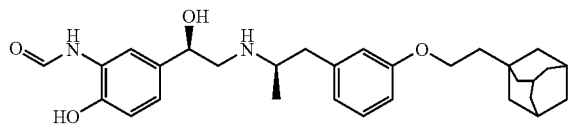

Obtained from Intermediate 68 (0.24 g, 0.41 mmol) and palladium on charcoal (10%, 0.04 g) by the same procedure described in Example 1 (reaction time: 2 hours). The crude was purified by column chromatography with silica gel, eluting with methylen chloride/methanol (form 98:2 to 90:10) to give the title compound as a solid (0.07 g, 38%).

$^1$H-NMR (300 MHz, CDCl3): 0.93 (d, J=6.05 Hz; 3H); 1.49-1.7 (m, 14H); 1.92 (bs, 3H); 2.39-2.75 (m, 4H); 2.89 (bs, 1H); 3.9 (t, J=7.14 Hz; 2H); 4.47 (bs, 1H); 6.68-6.88 (m, 6H); 7.14-7.16 (m, 1H); 8.03 (s, 1H); 8.26 (s, 1H); 9.55 (s, 1H).
MS (M+): 493.

Intermediate 69. 5-((1R)-2-[((1R)-2-{3-[2-(1-adamantyl)ethoxy]phenyl}-1-methylethyl)amino]-1-{[tert-butyl(dimethyl)silyl]oxy}ethyl)-8-(benzyloxy)-quinolin-2(1H)-one Obtained from Intermediate 66 (2.25 g, 7.18 mmol), (R)-8-(benzyloxy)-5-(2-bromo-1-(tert-butyldimethylsilyloxy)ethyl)quinolin-2(1H)-one (3.5 g, 7.16 mmol), sodium hydrogen carbonate (1.8 g, 21.55 mmol) and sodium iodide (3.2 g, 21.48 mmol) by the same procedure described in Intermediate 32 (reaction time: 1 hour). The crude was purified by column chromatography with silica gel, eluting with methylen chloride/methylen chloride:methanol (from 1% to 3%). The title compound was obtained as an oil (2 g, 39%).
MS (M+): 722.

Intermediate 70. 5-{(1R)-2-[((1R)-2-{3-[2-(1-adamantyl)ethoxy]phenyl}-1-methylethyl)amino]-1-hydroxyethyl}-8-(benzyloxy)quinolin-2(1H)-one Obtained from Intermediate 69 (2 g, 2.77 mmol) and tetrabutylammonium fluoride trihydrate (1.16 g, 4.44 mmol) by the same procedure described in Intermediate 33 (reaction time: 2 hours). The title compound was obtained as a foam (1.58 g, 94%) and used in the next step without further purification. MS (M+): 607.

Example 13

5-{(1R)-2-[((1R)-2-{3-[2-(1-adamantyl)ethoxy]phenyl}-1-methylethyl)amino]-1-hydroxyethyl}-8-hydroxyquinolin-2(1H)-one

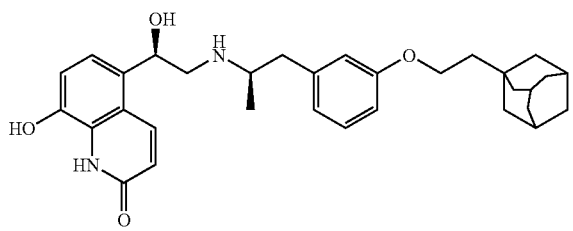

Obtained from Intermediate 70 (1.58 g, 2.6 mmol) and palladium on charcoal (10%, 0.28 g) by the same procedure described in Example 1 (reaction time: 2 hours). The crude obtained was purified by column chromatography with silica gel, eluting with methylen chloride/methanol (from 98:2 to 9:1) to give the title compound as a solid (0.83 g, 62%).

$^1$H-NMR (300 MHz, CDCl3): 0.92 (d, J=5.77 Hz, 3H); 1.47-1.69 (m, 14H); 1.92 (bs, 3H); 2.37-2.47 (m, 1H); 2.63-2.88 (m, 4H); 3.96 (t, J=7.14 Hz, 2H); 4.96 (bs, 1H); 6.49 (d, J=9.89 Hz, 1H); 6.65 (d, J=7.42 Hz, 1H); 6.71 (d, J=7.14 Hz, 1H); 6.89 (d, J=8.24 Hz, 1H); 7.03 (d, J=8.15 Hz, 1H); 7.11 (t, J=7.25 Hz, 1H); 8.15 (d, J=9.9 Hz, 1H).
MS (M+): 517.

Intermediate 71. methyl tricyclo[3.3.1.13,7]dec-2-ylideneacetate

To a solution of 2-adamantanone (5 g, 33.28 mmol) in 32 mL of methanol was added methyl 2-(diethoxyphosphoacetate) (9 mL, 49.68 mmol). The reaction mixture was cooled at 0° C. and into it was slowly added sodium methoxide (solution of 30% wt). The mixture was stirred overnight at room temperature. The solvent was removed under reduced pressure and the crude was treated with ethyl acetate and water. The organic layer was dried and the solvent was removed under reduced pressure. The crude was purified by column chromatography with silica gel, eluting with hexane/ethyl acetate (90:1) to give the title compound was obtained as a solid (6.41 g, 90%).

Intermediate 72. methyl 2-adamantylacetate

To a solution of Intermediate 71 (6.4 g, 31.07 mmol) in methanol (100 mL) was added ammonium formiate (7.8 g, 124.33 mmol), then under argon was added palladium on charcoal (0.6 g, 10%). The reaction mixture was stirred at room temperature for 3 hours. The catalyst was filtered through Celite® and the solvent removed under reduced pressure. The crude was treated with water and ethyl acetate, and the organic layer was extracted and the solvent was removed under reduced pressure. The title compound was obtained as an colourless iol (6.2 g, 95%).

Intermediate 73. 2-(2-adamantyl)ethanol

To a solution of lithium aluminium hydride (1.58 g, 41.63 mmol) in anhydrous tetrahydrofuran was slowly added a solution of Intermediate 72 (6.2 g, 29.76 mmol) in tetrahydrofuran (55 mL). The reaction mixture was stirred at room temperature overnight. Then water (12 mL), sodium hydroxide 4N (12 mL) and finally water again (36 mL) were added into the solution at 0° C. The mixture was stirred for some minutes and the resulting salts were filtered through a pad of Celite® washing with ethyl acetate (100 mL). The crude was treated with water and methylen chloride and the solvent of the organic layer was removed under reduced pressure to give the title compound as an oil (4.83 g, 90%), which was used in the next step without further purification.

Intermediate 74. 2-(2-adamantyl)ethyl methanesulfonate

Obtained from Intermediate 73 (2.4 g, 13.31 mmol), triethylamine (2.2 mL, 15.86 mmol) and methanesulfonyl chloride (1.24 mL, 16.02 mmol) by the same procedure described in Intermediate 44 (reaction time: overnight). The title compound was obtained as an oil (3.3 g, 95%) and used in the next step without further purification.

Intermediate 75. tert-butyl (2-{4-[2-(2-adamantyl) ethoxy]phenyl}ethyl)-carbamate Obtained from Intermediate 20 (0.45 g, 1.92 mmol), Intermediate 74 (0.64 g, 2.48 mmol) and cesium carbonate (0.82 g, 2.53 mmol) by the same procedure described in Intermediate 7. The title compound was obtained (0.77 g, 99%) and used in the next step without further purification. MS (M+): 400.

Intermediate 76. (2-{4-[2-(2-adamantyl)ethoxy] phenyl}ethyl)amine

Obtained from Intermediate 75 (0.788 g, 1.97 mmol) and hydrogen chloride 1.25 M in ethanol (26 mL) by the same procedure described in Intermediate 17. The title compound was obtained as a yellow solid (0.5 g, 84%) and used in the next step without further purification. MS (M+): 300.

Intermediate 77. 5-((1R)-2-[(2-{4-[2-(2-adamantyl) ethoxy]phenyl}ethyl)amino]-1-{[tert-butyl(dimethyl) silyl]oxy}ethyl)-8-(benzyloxy)quinolin-2(1H)-one Obtained from Intermediate 76 (0.5 g, 1.67 mmol), (R)-8-(benzyloxy)-5-(2-bromo-1-(tert-butyldimethylsilyloxy) ethyl)quinolin-2(1H)-one (0.81 g, 1.67 mmol), sodium hydrogen carbonate (0.27 g, 3.33 mmol) and sodium iodide (0.05 g, 0.33 mmol) by the same procedure described in Intermediate 32. The crude was purified by column chromatography with silica gel, eluting with methylen chloride/methanol (90:1) obtaining the title compound as a yellow solid (0.6 g, 51%). MS (M+): 708.

Intermediate 78. 5-{(1R)-2-[(2-{4-[2-(2-adamantyl) ethoxy]phenyl}ethyl)amino]-1-hydroxyethyl}-8-(benzyloxy)quinolin-2(1H)-one Obtained from Intermediate 77 (0.6 g, 0.85 mmol) and tetrabutylammonium fluoride trihydrate (0.46 g, 1.45 mmol) by the same procedure described in Intermediate 19. The crude was purified by column chromatography with silica gel, eluting with methylen chloride/methanol (90:4) to give the title compound as white foam (0.33 g, 66%). MS (M+): 593.

Example 14

5-{(1R)-2-[(2-{4-[2-(2-adamantyl)ethoxy] phenyl}ethyl)amino]-1-hydroxyethyl}-8-hydroxyquinolin-2(1H)-one

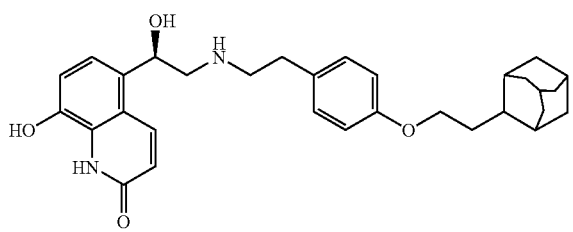

Obtained from Intermediate 78 (0.33 g, 0.57 mmol) and palladium on charcoal (34 mg, 0.32 mmol) by the same procedure described in Example 1. The crude was purified by column chromatograpy with silica gel, eluting with methylen chloride/methanol (from 20:1 to 10:1) obtaining the title compound as a white solid (0.15 g, 52%).

$^1$H-NMR (300 MHz, DMSO): 1.49 (d, J=12.09 Hz, 2H); 1.69-1.72 (m, 6H); 1.79-1.9 (m, 10H); 2.67-2.72 (m, 2H); 2.79-2.86 (m, 4H); 3.92-3.96 (m, 2H); 5.12 (bs, 1H); 6.52 (d, J=9.89 Hz, 1H); 6.83 (d, J=8.24 Hz, 2H); 6.93 (d, J=7.96 Hz, 1H); 7.08-7.1 (m, 3H); 8.18 (d, J=9.89 Hz, 1H).
MS (M+): 503.

Intermediate 79. tert-butyl (2-{3-[2-(2-adamantyl) ethoxy]phenyl}ethyl)-carbamate Obtained from Intermediate 29 (0.706 g, 2.98 mmol), Intermediate 74 (0.99 g, 3.83 mmol) and cesium carbonate (1.2 g, 3.87 mmol) by the same procedure described in Intermediate 7. The title compound was obtained as a solid (1.1 g, 99%) and used in the next step without further purification. MS (M+): 400.

Intermediate 80. (2-{3-[2-(2-adamantyl)ethoxy] phenyl}ethyl)amine

Obtained from Intermediate 79 (1.25 g, 3.13 mmol) and hydrogen chloride 1.25 M in methanol (40 mL) by the same procedure described in Intermediate 17 (reaction time: overnight). The title compound was obtained as a yellow oil (0.71 g, 76%) and used in the next step without further purification. MS (M+): 300.

Intermediate 81. 5-((1R)-2-({2-[3-(2-adamantyl-methoxy)phenyl]ethyl}amino)-1-{[tert-butyl(dimethyl)silyl]oxy}ethyl)-8-(benzyloxy)quinolin-2(1H)-one Obtained from Intermediate 80 (0.711 g, 2.37 mmol), (R)-8-(benzyloxy)-5-(2-bromo-1-(tert-butyldimethylsilyloxy) ethyl)quinolin-2(1H)-one (1.1 g, 2.37 mmol), sodium hydrogen carbonate (0.4 g, 4.76 mmol) and sodium iodide (70 mg, 0.47 mmol) by the same procedure described in Intermediate 32. The crude was purified by column chromatography with silica gel, eluting with methylen chloride/methanol (from 90:1 to 90:2) to obtain the title compound as a solid (0.712 g, 42%). MS (M+): 708.

Intermediate 82. 5-[(1R)-2-({2-[3-(2-adamantyl-methoxy)phenyl]ethyl}amino)-1-hydroxyethyl]-8-(benzyloxy)quinolin-2(1H)-one Obtained from Intermediate 81 (0.71 g, 1.01 mmol) and tetrabutylammonium fluoride trihydrate (0.54 g, 1.71 mmol) by the same procedure described in Intermediate 19. The crude was purified by column chromatography with silica gel, eluting with methylen chloride/methanol (90:4) to give the title compound as a solid (0.48 g, 81%).

Example 15

5-[(1R)-2-({2-[3-(2-adamantylethoxy)phenyl] ethyl}amino)-1-hydroxyethyl]-8-hydroxyquinolin-2 (1H)-one

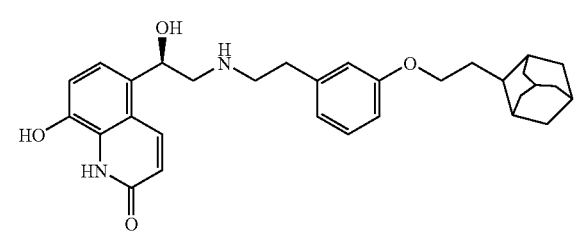

Obtained from Intermediate 82 (0.48 g, 0.82 mmol) and palladium on charcoal (50 mg, 10%) by the same procedure described in Example 1 (reaction time: 72 hours). The crude was purified by column chromatography with silica gel, eluting with methylen chloride/methanol (from 20:1 to 10:1) to give the title compound as a yellow pale solid (0.19 g, 46%).

¹H-NMR (300 MHz, DMSO): 1.49 (d, J=11.54 Hz, 2H); 1.69-1.90 (m, 16H); 2.63-2.79 (m, 6H); 3.93-3.97 (m, 2H); 5.01 (bs, 1H); 6.49 (d, J=9.89 Hz, 1H); 6.71-6.76 (m, 3H); 6.90 (d, J=8.24 Hz, 1H); 7.05 (d, J=8.24 Hz, 1H); 7.14 (t, J=7.97 Hz, 1H); 8.16 (d, J=9.89 Hz, 1H).

MS (M+): 503.

Intermediate 83. (R)—N—((R)-2-(tert-butyldimethylsilyloxy)-2-(2,2-dimethyl-4H-benzo[d][1,3]dioxin-6-yl)ethyl)-1-(3-(1-adamantyl)-ethoxyphenyl)propan-2-amine A mixture of 695 mg (2.21 mmol) of Intermediate 66, 710 mg (1.76 mmol) of (R)-(2-bromo-1-(2,2-dimethyl-4H-benzo[d][1,3]dioxin-6-yl)ethoxy)(tert-butyl)dimethylsilane (US 2004854829, ex 69e) and 186 mg (2.21 mmol) of sodium hydrogen carbonate in 8 ml of N-methyl-2-pyrrolidone is stirred at 120° C. for 10 hr. Excess water is added and the mixture is extracted 2 times with ethyl acetate. The organic layer is washed with water, dried and concentrated. The residue (1.4 g) is chromatographied on silica eluting with dichloromethane, then dichloromethane/methanol 100:1 to give 922 mg (68%) of a yellow oil.

Intermediate 84. N-(2-(hydroxy)-2-(2,2-dimethyl-4H-benzo[d][1,3]dioxin-6-yl)ethyl)-1-(3-(1-adamantyl)-ethoxyphenyl)propan-2-amine 928 mg (1.26 mmol) of the Intermediate 83 and 794 mg (2.52 mmol) of tetrabutylammonium fluoride trihydrate in 30 ml of anhydrous THF are stirred at room temperature overnight. The solution is concentrated and the residue is partitioned in ethyl acetate/water. The organic layer is washed with water, dried and concentrated. The residue is chromatographied on silicagel using dichloromethane/methanol 90:3 as eluent to give 590 mg (990% yield) of the desired compound as a yellowish oil.

Example 16

4-{(1R)-2-[((1R)-2-{3-[2-(1-adamantyl)ethoxy]phenyl}-1-methylethyl)amino]-1-hydroxyethyl}-2-(hydroxymethyl)phenol

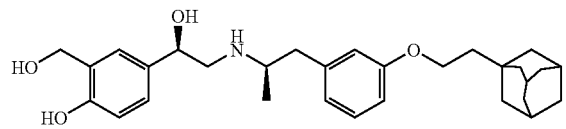

510 mg (0.99 mmol) of the Intermediate 84 in 5 ml of acetic acid and 2.5 ml of water are stirred at 80° C. for 1 hr. The solution is concentrated (with subsequent addition of cyclohexane in order to remove traces of acetic acid. The residue is chromatographied on silicagel eluting with dichloromethane/methanol/aqueous ammonia 90:5:0.5 to give 341 mg (69% yield) of the title compound as a colorless foam.

¹H-NMR (300 MHz, dimethylsulfoxide-D⁶): 1.07-1.10 (m, 3H) 1.56-1.70 (m, 15H); 1.97 (bs, 4H); 2.61-2.94 (m, 6H); 4.00 (t, J=6.59 Hz, 2H); 4.43-4.55 (m, 1H); 4.80 (s, 2H); 6.66-6.82 (m, 5H); 6.95 (bs, 1H); 7.11 (d, J=6.0 Hz, 1H); 7.15-7.21 (m, 2H); 7.26 (s, 2H).

MS (M+): 480.

Intermediate 85. Methyl 2,2-dimethyl-3-(3-(1-adamantyl)ethoxyphenyl) propanoate 4.05 g (19.45 mmol) of methyl 3-(3-hydroxyphenyl)-2,2-dimethylpropanoate (for preparation see WO03/082205 page 148) are solved in 40 ml DMF. 0.82 g of sodium hydride (60% suspension) are added in portions. After a 30 min stirring period at room temperature, a solution of 5.02 g (19.43 mmol) of intermediate 44 in 10 ml of DMF is added slowly. The solution is stirred at 60° C. for 16 hrs. The solvent is removed at reduced pressure and the residue partitioned between ethyl acetate and water. The organic layer is washed with water, dried and concentrated, giving 7.3 g of an oil that is used in the next step without further purification.

Intermediate 86. 2,2-Dimethyl-3-(3-(1-adamantyl)ethoxyphenyl) propionic acid 6.68 g (18.02 mmol) of the Intermediate 85 are dissolved in 300 ml of methanol. 30 ml of water and 50 ml of 2N NaOH solution are added and the system is stirred at 100° C. (bath temperature) for 4 hrs. The methanol is evaporated, excess water and 2N HCl to neutrality are added and the compound is extracted with ethyl acetate. The organic layer is washed with water, dried and concentrated. The residue (5.0 g) is used per se in the next step.

Intermediate 87. 1,1-Dimethyl-2-(3-(1-adamantyl) ethoxyphenyl)ethylamine 2.17 g (6.09 mmol) of the Intermediate 86 are dissolved in 200 ml of acetone. 1.95 ml (13.99 mmol) of triethylamine are added and the solution is cooled to 0° C. A solution of 0.89 ml (6.84 mmol) of isobutyl chloroformiate in 15 ml of acetone is dropped into the system. After 30' at 0° C. a solution of 0.99 g (15.23 mmol) of sodium azide in 10 ml of water is slowly added, and the stirring at 0° C. is prosecuted for an additional period of 30 min. Excess water is added, the system is extracted with ethyl ether which is washed with water, dried and concentrated at room temperature. The residue is dissolved in 15 ml of toluene and this solution added slowly to 150 ml of refluxing toluene. The reflux is prosecuted for an additional hour and the solution is concentrated. The residue is dissolved in 15 ml of dioxane, 35 ml of 5N HCl are added and the system is stirred at 100° C. for 30'. The solution is neutralised with 2N NaOH and is extracted with ethyl ether. The ethereal layer is washed with water, dried and concentrated. The residue is chromatographied on silicagel eluting with ethyl acetate/methanol 10:1 then 6:1 giving 1.46 g (72%) of yellowish oil.

Intermediate 88. 8-(benzyloxy)-5-(1-(tert-butyldimethylsilyloxy)-2-(2-methyl-1-(3-(2-(1-adamantyl) ethoxy)phenyl)propan-2-ylamino)ethyl)quinolin-2 (1H)-one To a solution of Intermediate 87 (0.981 g, 3.0 mmol) and (R)-8-(benzyloxy)-5-(2-bromo-1-(tert-butyldimethylsilyloxy)ethyl)quinolin-2(1H)-one (1.463 g, 2.99 mmol) in N-methylpyrrolidinone (5 mL) was added sodium iodide (0.471 g, 3.14 mmol) and sodium hydrogencarbonate (0.352 g, 4.19 mmol). The reaction mixture was heated at 120° C. for 4 hours and poured into excess water. The organic layer was extracted with diethyl ether and washed with water. The solvent was removed under reduced pressure and the crude was purified by column chromatography with silica gel, eluting with dichloromethane/methanol (from 90:1 to 90:2) to give 0.748 g (34% yield) of the title compound.

Intermediate 89. 8-(benzyloxy)-5-(1-(hydroxy)-2-(2-methyl-1-(3-(2-(1-adamantyl)ethoxy)phenyl)propan-2-ylamino)ethyl)quinolin-2(1H)-one To a solution of Intermediate 88 (0.748 g, 1.02 mmol) in tetrahydrofuran (15 mL) were added 0.546 g (1.73 mmol) of tetrabutylammonium fluoride. The reaction mixture was stirred at room temperature overnight. The solvent was removed under reduced pressure and the crude was partitioned between ethyl acetate and water. The organic layer was washed several times with water and the solvent was removed under reduced pressure. The crude was purified by column chromatography with silica gel, eluting with dichloromethane/methanol 90:4 to give 0.505 g (80% yield) of the title compound.

Example 17

5-{(1R)-2-[2-{3-[2-(1-adamantyl)ethoxy]phenyl}-1,1-dimethylethyl)amino]-1-hydroxyethyl}-8-hydroxyquinolin-2(1H)-one

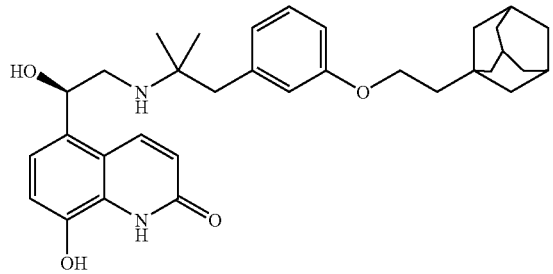

To a solution of Intermediate 89 (0.505 g, 0.81 mmol) in 15 ml of methanol was added palladium on charcoal (10%, 0.05 g). The mixture was hydrogenated under a balloon pressure at room temperature overnight. The catalyst was filtered and the solvent removed under reduced pressure. The crude was treated with ether to obtain the title compound as a yellow solid (0.43 g, 99%).

$^1$H-NMR (300 MHz, dimethylsulfoxide-D$^6$): 1.16 (s, 6H); 1.48-1.69 (m, 15H); 1.92 (bs, 2H); 2.50 (s, 1H); 2.87-2.99 (m, 4H); 3.98-4.02 (m, 2H); 5.40 (bs, 1H); 6.56 (d, J=9.8 Hz, 1H); 6.73-6.84 (m, 3H); 7.00 (d, J=8.1 Hz, 1H); 7.18-7.23 (m, 2H); 8.24 (d, J=9 Hz, 1H).

MS (M+): 531.

Test A
Human Adrenergic $\beta_1$ and $\beta_2$ Receptor Binding Assays

The study of binding to human adrenergic ($\beta_1$ and $\beta_2$ receptors was performed using commercial membranes prepared from Sf9 cells where they are overexpressed (Perkin Elmer).

The membrane suspensions (16 μg/well for $\beta_1$ and 5 μg/well for $\beta_2$) in assay buffer, 75 mM Tris/HCl with 12.5 mM MgCl2 and 2 mM EDTA pH=7.4, were incubated with 0.14 nM 3H-CGP12177 (Amersham) and different concentrations of the test compounds, in a final volume of 250 μl, in GFC Multiscreen 96 well plates (Millipore) pretreated with +0.3% PEI. Non specific binding was measured in the presence of 1 μM propanolol. Incubation was for 60 minutes at room temperature and with gentle shaking. The binding reactions were terminated by filtration and washing with 2.5 volumes of Tris/HCl 50 mM pH=7.4. The affinity of each test compound to the receptor was determined by using at least six different concentrations ran in duplicate. IC$_{50}$ values were obtained by non-linear regression using SAS.

Compounds of the present invention were found to have IC$_{50}$ values less than 5 nM for $\beta_2$ receptor and more than 60 nM for $\beta_1$ receptor, with $\beta_1/\beta_2$ ratios from 12 to 1500.

Test B
Determination of Agonist Activity and Offset of Action on Isolated Guinea-Pig Tracheal Rings (Resting Tone)
Test Compounds and Products The test compounds were dissolved in distilled water. Some of them needed to be dissolved using 10% polyethylene glycol 300 and a few drops of HCl 0.1 N. Isoprenaline hemisulfate (Sigma 15752) and dissolved in distilled water. Stock solutions were then diluted in Krebs Henseleit solution (NaCl 118 mM, KCl 4.7 mM, CaCl2 2.52 mM, MgSO4 1.66 mM, NaHCO3 24.9 mM, KH2PO4 1.18 mM, glucose 5.55 mM, sodium pyruvate 2 mM) to prepare different concentration ranges per each compound.

Experimental Procedure

The activity of compounds in tracheal ring was assessed according a previously described procedure (Cortijo et al., Eur J. Pharmacol. 1991, 198, 171-176). Briefly, adult, male guinea pigs (400-500 g) were sacrificed by a blow to the head with immediate exsanguinations (abdominal aorta). Tracheas were excised and placed into Krebs solution in a Petri dish. The adherent connective tissue was dissected away and the lumen gently flushed with Krebs solution. Each trachea was dissected into single rings. First, cotton thread was attached to the cartilage at both sides of the smooth muscle. The rings were opened by cutting through the cartilage on the side opposite to the smooth muscle band. Then, one end of the ring was attached to the strain gauge and the other end was attached to the organ-bath under a resting tension of 1 g and changes in tension of the rings were measured using an isometric transducer. The bath contained Krebs solution gassed with 5% CO2 in oxygen at 37° C. Tissues were then left for one hour to stabilize.

At the beginning of the experience, isoprenaline was administered at a concentration of 0.1 μM to test ring relaxation. Rings were then washed twice with Krebs solution and left to recover for 15-30 min. For each compound, a range of increasing and accumulative concentrations (0.01 nM to 0.1 μM) was administered with a maximum waiting time of 30 min between each administration. After the maximum concentration (achievement of complete relaxation), ring preparations were washed every 15 min during 1 hour. At the end of the experiment, 0.1 μM of isoprenaline was administered to each preparation to produce maximum relaxation back.

Determination of Agonist Activity and Offset of Action

Agonist activity was determined by assaying accumulative increasing concentrations of test compounds prepared in the Krebs solution. The magnitude of each response was measured and expressed as a percentage versus the maximum relaxation induced by isoprenaline. Potency values for the test compounds were expressed in absolute terms (concentration required to induce a 50% relaxation, EC50).

The time to 50% offset of action is defined as the time from the end of test compounds administration to attainment of 50% recovery. Recovery time was expressed as the percentage of recovery (loss of relaxation) reached 1 h after test compounds administration. Compounds of the present invention showed $EC_{50}$ values less than 5 nM with less than 3% recovery at 60 min.

Test C

Acetylcholine-Induced Bronchoconstriction in Guinea Pig

Test Compounds and Products

The test compounds were dissolved in distilled water. Some of them need to be dissolved using a maximum of 10% polyethylene glycol 300. Acetylcholine HCl was supplied by Sigma (code A 6625) and dissolved in saline solution.

Experimental Procedure

Male guinea-pigs (450-600 g) were supplied by Harlan (Netherlands), and maintained at a constant temperature of 22±2° C., humidity 40-70% with 10 cycles of room air per hour. They were illuminated with artificial light in 12 hour cycles (from 7 h am to 7 h pm). A minimum of 5 days acclimatization period was left before animals were dosed with test compounds. The animals were fasted 18 hours before the experiment with water ad libitum.

Guinea pigs were exposed to an aerosol of a test compound or vehicle. These aerosols were generated from aqueous solutions using a Devilbiss nebuliser (Model Ultraneb 2000, Somerset, Pa., SA). A mixture of gases ($CO_2$=5%, $O_2$=21%, $N_2$=74%) was flown through the nebuliser at 3 L/minute. This nebuliser was connected to a methacrylate box (17×17×25 cm) where the animals were placed one per session. Every guinea pig remained in the box for a total of 10 minutes. Aerosols were generated at 0 and 5 minutes during 60 seconds each one (approximately 5 mL of solution was nebulised).

Aerosol concentrations between 0.1 and 300 μg/ml of the compounds were administered. The bronchoprotective effects of test compounds were evaluated one hour or twenty four hours post-dose with a Mumed PR 800 system.

Determination of Bronchoprotective Effect and Calculations

The guinea pigs were anesthetized with an intramuscular injection of ketamine (43.75 mg/kg), xylazine (83.5 mg/kg), and acepromazine (1.05 mg/kg) at a volume of 1 ml/kg. After the surgical site was shaved, a 2-3 cm midline incision of the neck was made. The jugular vein was isolated and cannulated with a polyethylene catheter (Portex Ld.) to allow an intravenous bolus of acetylcoline (10 and 30 μg/kg iv) at 4-min intervals. The carotid artery was cannulated and the blood pressure was measured by a Bentley Tracer transducer. The trachea was dissected and cannulated with a teflon tube and connected at a pneumotachograph Fleisch for measuring the airflow. Animal was ventilated using an Ugo Basile pump, with a volume of 10 ml/kg at a rate of 60 breaths/min. The transpulmonary pressure was measured with an esophageal cannula (Venocath-14, Venisystems) connected to Celesco transducer. Once the cannulations were completed a Mumed pulmonary measurement computer program enabled the collection of pulmonary values. The baseline values were within the range of 0.3-0.9 mL/cm H2O for compliance and within the range of 0.1-0.199 cm H2O/mL per second for lung resistance (RL).

The bronchoprotective effect of inhaled compounds was determined with the concentration of the test compound causing a 50% of inhibition of bronchoconstriction (EC50) induced by acetylcholine at 30 μg/kg iv Determination of Duration of Action Selected compounds of this invention show long duration of action. Compounds of the present invention show a ratio $ED_{50}$ at 24 hr/$ED_{50}$ at 4 hr less than 6.

Pharmaceutical Compositions

The pharmaceutical formulations may conveniently be presented in unit dosage form and may be prepared by any of the methods well known in the art of pharmacy. All methods include the step of bringing the active ingredient(s) into association with the carrier. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, glycerine or water with flavouring or colouring agent.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the composition is in the form of a capsule, any routine encapsulation is suitable, for example using the aforementioned carriers in a hard gelatine capsule.

Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred.

Each capsule or cartridge may generally contain between 2 μg and 150 μg of each therapeutically active ingredient. Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (e.g. EP0069715) or disks (e.g. GB 2041763; EP 0424790; DE 4239402 and EP 0674533), rotatable cylinders (e.g. EP 0166294; GB 2165159 and WO 92/09322) and rotatable frustums (e.g. WO 92/00771), all having cavities which have to be filled with powder from the container. Other multi dose devices have measuring slides (e. g. U.S. Pat. No. 5,201,308 and WO 97/00703) or measuring plungers with a local or circumferential recess to displace a certain volume of powder from the container to a delivery chamber or an air conduit e.g. EP 0505321, WO 92/04068 and WO 92/04928.

Reproducible dose measuring is one of the major concerns for multi dose inhaler devices.

The powder formulation has to exhibit good and stable flow properties, because filling of the dose measuring cups or cavities is mostly under the influence of the force of gravity.

For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (e.g. WO 97/000703). For such semi-permanent multi dose inhalers with disposable drug containers, the requirements to prevent drug accumulation are even more strict.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with.

Such atomisers are described, for example, in PCT Patent Application No. W0 91/14468 and International Patent Application No. WO 97/12687, reference here being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient (s) and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant.

The aerosol composition may be excipient free or may optionally contain additional formulation excipients well known in the art such as surfactants eg oleic acid or lecithin and cosolvens eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10µ, preferably 2-5µ. Particles having a size above 20µ are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline.

Achieving a high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate.

Pressurized aerosol compositions will generally be filled into canisters fitted with a valve, especially a metering valve. Canisters may optionally be coated with a plastics material e.g. a fluorocarbon polymer as described in WO96/32150. Canisters will be fitted into an actuator adapted for buccal delivery.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit contains suitably from 1 µg to 100 µg, and preferably from 5 µg to 50 µg of a β2-agonist according to the invention.

The amount of each active which is required to achieve a therapeutic effect will, of course, vary with the particular active, the route of administration, the subject under treatment, and the particular disorder or disease being treated.

The active ingredients may be administered from 1 to 6 times a day, sufficient to exhibit the desired activity. Preferably, the active ingredients are administered once or twice a day.

The compositions of the invention can optionally comprise one or more additional active substances which are known to be useful in the treatment of respiratory disorders, such as PDE4 inhibitors, corticosteroids or glucocorticoids and/or anticholinergics.

Examples of suitable PDE4 inhibitors that can be combined with β2-agonists are denbufylline, rolipram, cipamfylline, arofylline, filaminast, piclamilast, mesopram, drotaverine hydrochloride, lirimilast, roflumilast, cilomilast, oglemilast, apremilast, 6-[2-(3,4-Diethoxyphenyl)thiazol-4-yl]pyridine-2-carboxylic acid (tetomilast), (R)-(+)-4-[2-(3-Cyclopentyloxy-4-methoxyphenyl)-2-phenylethyl]pyridine, N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)adenine, N-(3,5-Dichloro-4-pyridinyl)-8-methoxyquinoline-5-carboxamide, N-[9-Methyl-4-oxo-1-phenyl-3,4,6,7-tetrahydropyrrolo[3,2,1-jk][1,4]benzodiazepin-3(R)-yl]pyridine-4-carboxamide, 3-[3-(Cyclopentyloxy)-4-methoxybenzyl]-6-(ethylamino)-8-isopropyl-3H-purine hydrochloride, 4-[6,7-Diethoxy-2,3-bis(hydroxymethyl) naphthalen-1-yl]-1-(2-methoxyethyl)pyridin-2(1H)-one, 2-carbomethoxy-4-cyano-4-(3-cyclopropylmethoxy-4-di fluororomethoxyphenyl)cyclohexan1-one, cis [4-cyano-4-(3-cyclopropylmethoxy-4-difluoromethoxyphenyl)cyclohexan-1-ol, ONO-6126 (Eur Respir J 2003, 22 (Suppl. 45): Abst 2557) and the compounds claimed in the PCT patent applications number WO03/097613, WO2004/058729, WO 2005/049581, WO 2005/123693 and WO 2005/123692

Examples of suitable corticosteroids and glucocorticoids that can be combined with β2-agonists are prednisolone, methylprednisolone, dexamethasone, Dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, Butixocort propionate, RPR-106541, halometasone, methylprednisolone suleptanate, mometasone furoate, rimexolone, prednisolone farnesylate, ciclesonide, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Examples of suitable M3 antagonists (anticholinergics) that can be combined with β2-agonists are tiotropium salts, oxitropium salts, flutropium salts, ipratropium salts, glycopyrronium salts, trospium salts, revatropate, espatropate, 3-[2-Hydroxy-2,2-bis(2-thienyl)acetoxy]-1-(3-phenoxypropyl)-1-azoniabicyclo[2.2.2]octane salts, 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl)piperidin-1-yl]-2(R)-[3,3-difluorocyclopent-1(R)-yl]-2-hydroxy-2-phenylethan-1-one (Banyu-280634), N—[N-[2-[N-[1-(Cyclohexylmethyl)piperidin-3(R)-ylmethyl]carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), UCB-101333, Merck's OrM3, 7-endo-(2-hydroxy-2,2-diphenylacetoxy)-9,9-dimethyl-3-oxa-9-azoniatricyclo[3.3.1.0(2,4)]nonane salts, 7-(2, 2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts chlorides, bromides, iodides and methanesulphonates are preferred.

Particularly preferred pharmaceutical composition according to the invention comprises a compound of formula (I) and a therapeutically effective amount of one or more additional therapeutic agents selected from the group consisting of mometasone furoate, ciclesonide, budesonide, fluticasone propionate, fluticasone furoate, tiotropium salts, glycopyrronium salts, 3-[2-Hydroxy-2,2-bis(2-thienyl)acetoxy]-1-(3-phenoxypropyl)-1-azoniabicyclo[2.2.2]octane salts, 1-(2-Phenylethyl)-3-(9H-xanthen-9-ylcarbonyloxy)-1-azoniabicyclo[2.2.2]octane salts, rolipram, roflumilast, cilomilast and the compounds claimed in the PCT patent applications number WO03/097613, WO2004/058729, WO 2005/049581, WO 2005/123693 and WO 2005/123692

Thus, in one aspect of the invention, the composition comprises a compound of formula (I) and a corticosteroid. Particularly preferred corticosteroids are those selected from the group consisting of mometasone furoate, ciclesonide, budesonide, fluticasone furoate and fluticasone propionate.

In another aspect of the invention, the composition comprises a compound of formula (I) and an anticholinergic agent. Particularly preferred anticholinergic agents are those selected from the group consisting of tiotropium salts, glycopirronium salts, 3-[2-Hydroxy-2,2-bis(2-thienyl)acetoxy]-1-(3-phenoxypropyl)-1-azoniabicyclo[2.2.2]octane salts and 1-(2-Phenylethyl)-3-(9H-xanthen-9-ylcarbonyloxy)-1-azoniabicyclo[2.2.2]octane salts. The composition may further comprise a corticosteroid selected from the group consisting of mometasone furoate, ciclesonide, budesonide, fluticasone furoate and fluticasone propionate.

In a still other aspect of the invention, the composition comprises a compound of formula (I) and a PDE4 inhibidor. Particularly preferred PDE4 inhibidors are those selected from the group consisting of rolipram, roflumilast, cilomilast and the compounds claimed in the PCT patent applications number WO03/097613, WO2004/058729, WO 2005/049581, WO 2005/123693 and WO 2005/123692. The composition may further comprise a corticosteroid selected from the group consisting of mometasone furoate, ciclesonide, budesonide, fluticasone furoate and fluticasone propionate. In addition to the compound of the invention and to the PDE4 inhibitor, the composition may further comprise an anticholinergic agent selected from the group consisting of tiotropium salts, glycopirronium salts, 3-[2-Hydroxy-2,2-bis(2-thienyl)acetoxy]-1-(3-phenoxypropyl)-1-azoniabicyclo [2.2.2] octane salts and 1-(2-Phenylethyl)-3-(9H-xanthen-9-ylcarbonyloxy)-1-azoniabicyclo[2.2.2] octane salts.

In a preferred embodiment of the present invention, the composition comprises a compound of formula (I) and a therapeutically effective amount of a 3-[2-Hydroxy-2,2-bis (2-thienyl)acetoxy]-1-(3-phenoxypropyl)-1-azoniabicyclo [2.2.2]octane salts. Optionally, the composition further comprises a corticosteroid and/or a PDE4 inhibitor.

In another preferred embodiment of the present invention, the composition comprises a compound of formula (I) and a therapeutically effective amount of a mometasone furoate. Optionally, the composition further comprises an anticholinergic salt and/or a PDE4 inhibitor.

In another embodiment of the invention, the composition comprises a compound of formula (I), a corticosteroid, an anticholinergic agent and a PDE4 inhibitor.

The combinations of the invention may be used in the treatment of respiratory diseases, wherein the use of bronchodilating agents is expected to have a beneficial effect, for example asthma, acute or chronic bronchitis, emphysema, or Chronic Obstructive Pulmonary Disease (COPD).

The active compounds in the combination, i.e. the β2-agonist of the invention and the PDE4 inhibitors, corticosteroids or glucocorticoids and/or anticholinergics may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The active substance compositions according to the invention are preferably administered in the form of compositions for inhalation delivered with the help of inhalers, especially dry powder inhalers, however, any other form or parenteral or oral application is possible. Here, the application of inhaled compositions embodies the preferred application form, especially in the therapy of obstructive lung diseases or for the treatment of asthma.

Additional suitable carriers for formulations of the active compounds of the present invention can be found in Remington: The Science and Practice of Pharmacy, 20th Edition, Lippincott Williams & Wilkins, Philadelphia, Pa., 2000. The following non-limiting examples illustrate representative pharmaceutical compositions of the invention.

Formulation Example 1

Oral Suspension

| Ingredient | Amount |
| --- | --- |
| Active Compound | 3 mg |
| Citric acid | 0.5 g |
| Sodium chloride | 2.0 g |
| Methyl paraben | 0.1 g |
| Granulated sugar | 25 g |
| Sorbitol (70% solution) | 11 g |
| Veegum K | 1.0 g |
| Flavoring | 0.02 g |
| Dye | 0.5 mg |
| Distilled water | q.s. to 100 mL |

Formulation Example 2

Hard Gelatine Capsule for Oral Administration

| Ingredient | Amount |
| --- | --- |
| Active Compound | 1 mg |
| Lactose | 150 mg |
| Magnesium stearate | 3 mg |

Formulation Example 3

Gelatin Cartridge for Inhalation

| Ingredient | Amount |
| --- | --- |
| Active Compound (micronized) | 0.2 mg |
| Lactose | 25 mg |

Formulation Example 4

Formulation for Inhalation with a DPI

| Ingredient | Amount |
| --- | --- |
| Active Compound (micronized) | 15 mg |
| Lactose | 3000 mg |

Formulation Example 5

Formulation for a MDI

| Ingredient | Amount |
| --- | --- |
| Active Compound (micronized) | 10 g |
| 1,1,1,2,3,3,3-heptafluoro-n-propane | q.s. to 200 ml |

The invention claimed is:

1. A compound of formula (I):

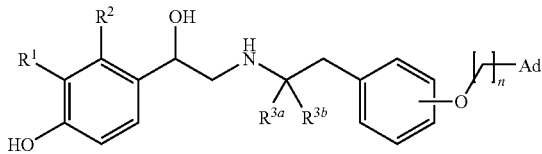

Formula (I)

wherein:
R¹ together with R² form the group —NH—C(O)—CH=CH—, wherein the nitrogen atom is bound to the carbon atom in the phenyl ring holding R¹ and the carbon atom is bound to the carbon atom in the phenyl ring holding R²
$R^{3a}$ and $R^{3b}$ are independently chosen from hydrogen atoms and $C_{1-4}$ alkyl groups,
n represents an integer from 1 to 3;
Ad represents a 1-adamantyl or 2-adamantyl group,
or a pharmaceutically-acceptable salt or stereoisomer thereof.

2. The compound according to claim 1, wherein R¹ together with R² form the group —NH—C(O)—CH=CH—, wherein the nitrogen atom in —NH—C(O)—CH=CH— is bound to the carbon atom in the phenyl ring holding R¹ and the carbon atom in —NH—C(O)—CH=CH—is bound to the carbon atom in the phenyl ring holding R².

3. The compound according to claim 1, wherein $R^{3a}$ and $R^{3b}$ are independently chosen from hydrogen atoms and methyl groups.

4. The compound according to claim 3, wherein $R^{3a}$ represents a hydrogen atom and $R^{3b}$ is chosen from a hydrogen atom and a methyl group.

5. The compound according to claim 1, wherein n has a value of 1 or 2.

6. The compound according to claim 5, wherein n has a value of 2.

7. The compound according to claim 1 of formula (IA):

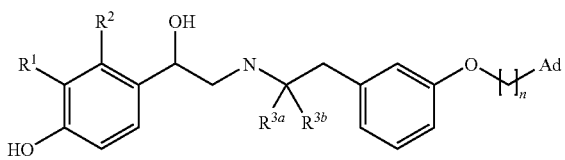

(IA)

wherein R¹, R², $R^{3a}$, $R^{3b}$, n and Ad are as defined in claim 1.

8. The compound according to claim 1 of formula (IA):

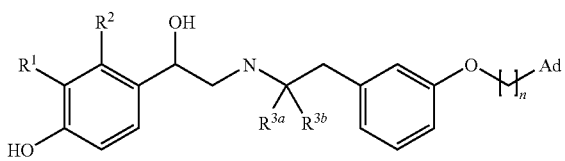

(IA)

wherein:
R¹ together with R² form the group —NH C(O)—CH=CH—, wherein the nitrogen atom in —NH—C(O)—CH=CH— is bound to the carbon atom in the phenyl ring holding R¹ and the carbon atom in —NH—C(O)—CH=CH— is bound to the carbon atom in the phenyl ring holding R²,
$R^{3a}$ represents a hydrogen atom and $R^{3b}$ is chosen from a hydrogen atom and a methyl group, and
n has a value of 2.

9. The compound according to claim 1, chosen from:
5-{(1R)-2-[((1R,S)-2-{3-[2-(1-adamantyl)ethoxy]phenyl}-1-methylethyl)amino]-1-hydroxyethyl}-8-hydroxyquinolin-2(1H)-one,
5-{(1R)-2-[(2-{4-[2-(1-adamantyl)ethoxy]phenyl}-1-methylethyl)amino]-1-hydroxyethyl}-8-hydroxyquinolin-2(1H)-one,
5-{(1R)-2-[(2-{4-[2-(1-adamantyl)ethoxy]phenyl}ethyl)amino]-1-hydroxyethyl}-8-hydroxyquinolin-2(1H)-one,
5-{(1R)-2-[(2-{3-[2-(1-adamantyl)ethoxy]phenyl}ethyl)amino]-1-hydroxyethyl}-8-hydroxyquinolin-2(1H)-one,
5-[(1R)-2-({2-[4-(1-adamantylmethoxy)phenyl]ethyl}amino)-1-hydroxyethyl]-8-hydroxyquinolin-2(1H)-one,
5-[(1R)-2-({2-[3-(1-adamantylmethoxy)phenyl]ethyl}amino)-1-hydroxyethyl]-8-hydroxyquinolin-2(1H)-one,
5-{(1R)-2-[(2-{3-[3-(1-adamantyl)propoxy]phenyl}ethyl)amino]-1-hydroxyethyl}-8-hydroxyquinolin-2(1H)-one,
5-{(1R)-2-[(2-{4-[2-(2-adamantyl)ethoxy]phenyl}ethyl)amino]-1-hydroxyethyl}-8-hydroxyquinolin-2(1H)-one,
5-[(1R)-2-({2-[3-(2-adamantylethoxy)phenyl]ethyl}amino)-1-hydroxyethyl]-8-hydroxyquinolin-2(1H)-one, and
5-{(1R)-2-[(2-{3-[2-(1-adamantyl)ethoxy]phenyl}-1,1-dimethylethyl)amino]-1-hydroxyethyl}-8-hydroxyquinolin-2(1H)-one,
or a pharmaceutically-acceptable salt thereof.

10. A pharmaceutical composition comprising a therapeutically effective amount of a compound according to claim 1 and a pharmaceutically acceptable carrier.

11. The pharmaceutical composition according to claim 10, wherein the composition further comprises a therapeutically effective amount of at least one other therapeutic agent.

12. The pharmaceutical composition according to claim 11, wherein the at least one other therapeutic agent is chosen from a corticosteroid, an antichlolinergic agent, and a PDE4 inhibitor.

13. The pharmaceutical composition according to claim 10, wherein the composition is formulated for administration by inhalation.

* * * * *